(12) United States Patent
Chen

(10) Patent No.: US 10,344,003 B2
(45) Date of Patent: Jul. 9, 2019

(54) SMALL MOLECULE FIEL1 INHIBITOR IN INFLAMMATORY AND FIBROTIC LUNG INJURY

(71) Applicant: UNIVERSITY OF PITTSBURGH—OF THE COMMONWEALTH SYSTEM OF HIGHER EDUCATION, Pittsburgh, PA (US)

(72) Inventor: Beibei Chen, Wexford, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 0 days.

(21) Appl. No.: 15/567,959

(22) PCT Filed: Apr. 21, 2016

(86) PCT No.: PCT/US2016/028614
§ 371 (c)(1),
(2) Date: Oct. 19, 2017

(87) PCT Pub. No.: WO2016/172325
PCT Pub. Date: Oct. 27, 2016

(65) Prior Publication Data
US 2018/0141916 A1    May 24, 2018

Related U.S. Application Data

(60) Provisional application No. 62/151,158, filed on Apr. 22, 2015.

(51) Int. Cl.
*A61K 31/4184*    (2006.01)
*C07D 235/26*    (2006.01)
*A61K 45/06*    (2006.01)
*A61P 11/06*    (2006.01)

(52) U.S. Cl.
CPC ........ *C07D 235/26* (2013.01); *A61K 31/4184* (2013.01); *A61K 45/06* (2013.01); *A61P 11/06* (2018.01)

(58) Field of Classification Search
CPC .................................................. A61K 31/4184
See application file for complete search history.

(56) References Cited

U.S. PATENT DOCUMENTS

2008/0262004 A1    10/2008    Diefenbacher et al.

FOREIGN PATENT DOCUMENTS

| CN | 102757370 A | 10/2012 |
|---|---|---|
| WO | WO 2006/017214 A2 | 2/2006 |
| WO | WO 2009/009059 A1 | 1/2009 |

OTHER PUBLICATIONS

International Preliminary Report on Patentability issued in related International Patent Application No. PCT/US2016/028614, dated Nov. 2, 2017.
International Search Report and Written Opinion issued in related International Patent Application No. PCT/US2016/028614, dated Aug. 10, 2016.
Attisano et al., "SMADS as Transcriptional o-modulators," *Current opinion in cell biology*, 12(2): 235-243 (2000).
Annes et al., "Making sense of latent TGFβ activation," *Journal of cell science*, 116(Pt 2): 217-224 (2003).
Bodor, N., "Novel Approaches in Prodrug Design," *Drugs of the Future*, vol. 6, pp. 165-182 (1981).
Bonniaud et al., "TGF-beta and Smad3 signaling link inflammation to chronic fibrogenesis," *Journal of immunology*, 175(8): 5390-5395 (2005).
Bundgaard, H., "Design of Prodrugs: Bioreversible-Derivatives for Various Functional Groups and Chemical Entities," in Design of Prodrugs, Elsevier (1985), 1 page Abstract.
Butler et al. "Cross-talk between Remodeling and de Novo Pathways Maintains Phospholipid Balance through Ubiquitination," *J. Biol. Chem.* 2010, 185(9): 6246-6258.
Chen et al., "Calmodulin Binds and Stabilizes the Regulatory Enzyme, CTP: Phosphocholine Cytidylyltransferase," *J. of Biol. Chem.*, 282(46):33494-33506 (2007).
Derynck et al., "SMAD-dependent and SMAD-independent pathways in TGF-beta family signaling," *Nature*, 425(6958): 577-584 (2003).
Gross et al., "Distinct effects of PIAS proteins on androgen-mediated gene activation in prostate cancer cells," *Oncogene*, 20(29): 3880-3887 (2001).
Hatakeyama et al., "U box proteins as a new family of ubiquitin-protein ligases," *J Biol Chem*, 276(35): 33111-33120 (2001).
Hecker et al., "NAPDH oxidase-4 mediates myofibroblast activation and fibrogenic responses to lung injury," *Nature medicine*, 15(9): 1077-1081 (2009).
Huibregtse et al., "A family of proteins structurally and functionally related to the E6-AP ubiquitin-protein ligase," *Proceedings of the National Academy of Sciences of the United States of America*, 92(7): 2563-2567 (1995).
Imoto et al., "Regulation of transforming growth factor-beta signaling by protein inhibitor of activated STAT, PIASy through Smad3," *The Journal of biological chemistry*, 278(36): 34253-34258 (2003).
Imoto et al., "The RING domain of PIASy is involved in the suppression of bone morphogenetic protein-signaling pathway," *Biochemical and biophysical research communications*, 319(1): 275-282 (2004).
Imoto et al., "Sumoylation of SMAD3 stimulates its nuclear export during PIASy-mediated suppression of TGF-beta signaling," *Biochem Biophys Res Commun*, 370(2): 359-365 (2008).
Jiang et al., Inhibition of pulmonary fibrosis in mice by CXCL10 requires glycosaminoglycan binding and syndecan-4, *J. Clinical investigation*, 120(6):2049-2057 (2010).

(Continued)

*Primary Examiner* — Brian E McDowell
(74) *Attorney, Agent, or Firm* — Foley & Lardner LLP

(57) ABSTRACT

Novel compounds are disclosed along with methods of inhibiting the TGFβ pathway and methods of treating Idiopathic Pulmonary Fibrosis (IPF) using such compounds.

9 Claims, 20 Drawing Sheets

(56) References Cited

OTHER PUBLICATIONS

Jin et al., "Dual E1 activation systems for ubiquitin differentially regulate E2 enzyme charging," *Nature*, 447(7148): 1135-1138 (2007).

Jonk et al., "Identification and functional characterization of a SMAD binding element (SBE) in the JunB promoter that acts as a transforming growth factor-beta, activin, and bone morphogenetic protein-inducible enhancer," *The Journal of biological chemistry*, 273(33): 21145-21152 (1998).

Kage et al., "EMT and interstitial lung disease: a mysterious relationship," *Current opinion in pulmonary medicine*, 18(5): 517-523 (2012).

Kamadurai, et al.,"Insights into Ubiquitin Transfer Cascades from a Structure of a UbcH5B-Ubiquitin-HECT$^{NEDD4L}$ Complex," *Molecular cell*, 36(6): 1095-1102 (2009).

Kesava et al., "A Simplified Method for the Analysis of Hydroxyproline in Biological Tissues," *Clinical Biochemistry*, 29(3): 225-229 (1996).

Kim et al., "Identification of a novel anti-apoptotic E3 ubiquitin ligase that ubiquitinates antagonists of inhibitor of apoptosis proteins SMAC, HtrA2, and ARTS," *J Biol Chem*, 288(17): 12014-12021 (2013).

Lee et al., "Sumoylation of SMAD4, the common Smad mediator of transforming growth factor-beta family signaling," *The Journal of biological chemistry*, 278(30): 27853-27863 (2003).

Long et al., "Repression of SMAD transcriptional activity by PIASy, an inhibitor of activated STAT," *Proceedings of the National Academy of Sciences of the United States of America*, 100(17): 9791-9796 (2003).

Neuman et al., "The Determination of Hydroxyproline," *J. of Biol. Chem.*, 184(1): 299-306 (1950).

Notari, "Theory and Practice of Prodrug Kinetics," *Methods in Enzymology*, vol. 112, pp. 309-323 (1985).

Ray et al., "Dynamic regulation of cardiolipin by the lipid pump, ATP8b1, determines the severity of lung injury in experimental bacterial pneumonia," *Nat. Med.*, 16(10): 1120-1127 (2010).

Rotin et al., "Physiological functions of the HECT family of ubiquitin ligases," *Nature reviews Molecular cell biology*, 10(6): 398-409 (2009).

Rytinki et al., "PIAS proteins: pleiotropic interactors associated with SUMO," *Cell Mol Life Sci*, 66(18): 3029-3041 (2009).

Tager et al., "The lysophosphatidic acid receptor LPA1 links pulmonary fibrosis to lung injury by mediating fibroblast recruitment and vascular leak," *Nat. Med.*, 14(1):45-54 (2008).

Tanaka et al., "c-Cbl-dependent monoubiquitination and lysosomal degradation of gp130," *Mol Cell Biol*, 28(15): 4805-4818 (2008).

Umadevi N et al. *Acta crystallographica Section F, Structural biology and crystallization communications*, 61(Pt 12): 1084-1086 (2005).

Wang et al., "Caveolin-1: a critical regulator of lung fibrosis in idiopathic pulmonary fibrosis," *The Journal of experimental medicine*, 203(13): 2895-2906 (2006).

Yingling et al., "Development of TGF-beta signaling inhibitors for cancer therapy," *Nature reviews Drug discovery*, 3(12): 1011-1022 (2004).

SMALL MOLECULE FIEL1 INHIBITOR IN INFLAMMATORY AND FIBROTIC LUNG INJURY

CROSS REFERENCE TO RELATED APPLICATION

This application is a National Stage of International Patent Application No. PCT/US2016/028614, filed Apr. 21, 2016, which claims priority to U.S. Provisional Patent Application No. 62/151,158, filed Apr. 22, 2015. The contents of these applications are incorporated herein, by reference in their entirety.

STATEMENT OF GOVERNMENT SUPPORT

This invention was made with government support under NIH grant #HL116472 awarded by the NIH. The government has certain rights in the invention.

BACKGROUND

An aspect of the present invention relates generally to the field of compounds and treatment of diseases associated with an activated inflammatory pathway or idiopathic pulmonary fibrosis (IPF).

IPF is a progressive fibrotic disease characterized by massive neovascularization and deposition of extracellular matrix into the interstitium. IPF is the most common form of interstitial lung disease with a prevalence of 50 per 100,000 cases, and it almost exclusively affects patients older than 50. Despite its unknown etiology, the downstream effectors of IPF are well-characterized. Samples from IPF patients show increased levels of transforming growth factor beta (TGFβ) across all three isoforms (Annes et al., "Making sense of latent TGFβ activation," *Journal of cell science*, 116(Pt 2): 217-224 (2003)). TGFβ serves as a critical pro-inflammatory molecule via the induction of neutrophil chemotaxis, the activation of epithelial to mesenchymal transition, and the promotion of lung epithelial cell apoptosis (Kage et al., "EMT and interstitial lung disease: a mysterious relationship," *Current opinion in pulmonary medicine*, 18(5): 517-523 (2012)). The TGFβ signaling pathway proceeds in part through the mothers against decapentaplegic homolog (SMAD) protein family. SMAD proteins regulate a variety of cellular processes, such as differentiation, proliferation, tumorogenesis, and immune responses (Attisano et al., "SMADS as transcriptional co-modulators," *Current opinion in cell biology*, 12(2): 235-243 (2000); Yingling et al., "Development of TGF-beta signalling inhibitors for cancer therapy," *Nature reviews Drug discovery*, 3(12): 1011-1022 (2004); Bonniaud et al., "TGF-beta and Smad3 signaling link inflammation to chronic fibrogenesis," *Journal of immunology*, 175(8): 5390-5395 (2005)). The SMAD family is comprised of receptor-SMADs (R-SMAD), inhibitor SMADs (I-SMAD), and the common mediator SMAD (co-SMAD) (Deiynck et al., "SMAD-dependent and SMAD-independent pathways in TGF-beta family signaling," *Nature*, 425(6958): 577-584 (2003)). Briefly, TGFβ signal transduction commences with the phosphorylation of R-SMADs, often SMAD2 or SMAD3, which form a trimeric structure with the co-SMAD. SMAD4, and translocate to the nucleus to bind to the SMAD binding element (SBE) in the JunB promoter to activate transcription (Jonk et al., "Identification and functional characterization of a SMAD binding element (SBE) in the JunB promoter that acts as a transforming growth factor-beta, activin, and bone morphogenetic protein-inducible enhancer," *The Journal of biological chemistry*, 273 (33): 21145-21152 (1998)). Therefore, TGFβ is a major pro-fibrotic growth factor through the downstream SMAD signaling pathway (Wang et al., "Caveolin-1: a critical regulator of lung fibrosis in idiopathic pulmonary fibrosis," *The Journal of experimental medicine*, 203(13): 2895-2906 (2006); Hecker et al., "NADPH oxidase-4 mediates myofibroblast activation and fibrogenic responses to lung injury," *Nature medicine*, 15(9): 1077-1081 (2009)).

PIAS (protein inhibitor of activated STAT) proteins are a family of proteins that are known to negatively control and regulate gene transcription and inflammatory pathways in cells (Rytinki et al., "PIAS proteins: pleiotropic interactors associated with SUMO," *Cell Mol Life Sci*, 66(18): 3029-3041 (2009)). There are four characterized PIAS family members, PIAS1, PIASx (PIAS2), PIAS3, and PIASy (PIAS4), each with specificity toward different pathways (Gross et al., "Distinct effects of PIAS proteins on androgen-mediated gene activation in prostate cancer cells," *Oncogene*, 20(29): 3880-3887 (2001)). Specifically, PIAS4 has been shown to suppress TGFβ signaling (Long et al., "Repression of SMAD transcriptional activity by PIASy, an inhibitor of activated STAT," *Proceedings of the National Academy of Sciences of the United States of America*, 100(17): 9791-9796 (2003); Imoto et al., "Regulation of transforming growth factor-beta signaling by protein inhibitor of activated STAT, PIASy through Smad3," *The Journal of biological chemistry*, 278(36): 34253-34258 (2003)). First, TGFβ promotes PIAS4's interaction with SMAD3 and SMAD4 to form a ternary complex PIAS4 is known to possess small ubiquitin-like modifier (SUMO) E3 ligase activity within its RING-type domain (Imoto et al., "The RING domain of PIASy is involved in the suppression of bone morphogenetic protein-signaling pathway," *Biochemical and biophysical research communications*, 319(1): 275-282 (2004)), so it promotes the sumoylation of SMAD3, in turn stimulating its nuclear export and inhibiting SMAD3/4 driven transcription (Imoto et al., "Sumoylation of SMAD3 stimulates its nuclear export during PIASy-mediated suppression of TGF-beta signaling," *Biochem Biophys Res Commun*, 370(2): 359-365 (2008); Lee et al., "Sumoylation of SMAD4, the common Smad mediator of transforming growth factor-beta family signaling," *The Journal of biological chemistry*, 278(30): 27853-27863 (2003)). Furthermore, PIAS4 directly recruits and interacts with histone deacetylase 1 (HDAC1) to repress SMAD3 driven transcriptional activation. In all, PIAS4 is an important negative regulator of TGFβ signaling.

Protein ubiquitination is the major protein processing function in cells. Ubiquitin (Ub) flags a targeted protein for degradation through the 26 s proteasome or lysosome (Tanaka et al., "c-Cbl-dependent monoubiquitination and lysosomal degradation of gp130," *Mol Cell Biol.*, 28(15): 4805-4818 (2008)). Ubiquitin is conjugated to a target protein in a three-step process. First, an E1 ubiquitin-activating enzyme binds to ubiquitin via a thioester covalent bond. Then, the E1 transfers the ubiquitin to an E2 ubiquitin-conjugating enzyme. Finally, the C-terminus of Ub is attached to the ε-amino lysine (K) residue of the substrate, mediated by a ubiquitin E3 ligase. There are several families of these ubiquitin E3 ligases that include over 1,000 proteins (Jin et al., "Dual E1 activation systems for ubiquitin differentially regulate E2 enzyme charging," *Nature*, 447(7148): 1135-1138 (2007); Hatakeyama et al., "U box proteins as a new family of ubiquitin-protein ligases," *J Biol Chem*, 276(35): 33111-33120 (2001)). Of these, the E6-AP Carboxyl Terminus (HECT) domain E3 ligase family remains poorly characterized (Rotin et al., "Physiological functions of the HECT family of ubiquitin ligases," *Nature reviews Molecular cell biology*, 10(6): 398-409 (2009)). There are ~30 HECT E3 ligases in mammalian cells, and functional data is only available for a select few including E6AP, Smurf, and NEDD4. HECT E3 ligases possess a unique feature in which they accept ubiquitin from an E2 ubiquitin-conjugating enzyme in the form of a thioester bond and directly transfer the ubiquitin to the substrate. An active site within the C-terminal of the HECT domain containing a cysteine residue is required for ubiquitin-thiolester formation (Huibregtse et al., "A family of proteins structurally and functionally related to the E6-AP ubiquitin-protein ligase," *Proceedings of the National Academy of Sciences of the United States of America*, 92(7): 2563-2567 (1995)). A recently identified member of the HECT E3 ligases, AREL1 encoded by the KIAA0317 gene, regulates the ubiquitination of the apoptosis proteins SMAC, HtrA2, and ARTS (Kim et al., "Identification of a novel anti-apoptotic E3 ubiquitin ligase that ubiquitinates antagonists of inhibitor of apoptosis proteins SMAC, HtrA2, and ARTS," *J Biol Chem*, 288(17): 12014-12021 (2013)).

Thus, there remains a need in the art to discover the role of the protein encoded by KIAA0317 in various signaling pathways. Futhermore, there remains a need in the art to develop new antagonists that exert potent anti-fibrotic activity for treating idiopathic pulmonary fibrosis (IPF). The present invention satisfies these needs.

SUMMARY OF THE INVENTION

One embodiment of the invention relates to a compound represented by Formula (I):

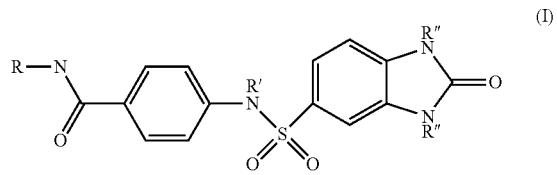

(I)

wherein R is

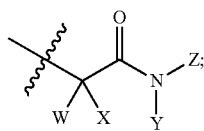

and wherein: (1) W is selected from the group consisting of H, optionally-substituted alkyl, optionally-substituted alkoxy, optionally-substituted aryl, optionally-substituted cycloalkyl, optionally-substituted heterocyclic, halogen, amino, and hydroxy; (2) X is selected from the group consisting of H, optionally-substituted alkyl, optionally-substituted alkoxy, optionally-substituted aryl, optionally-substituted cycloalkyl, optionally-substituted heterocyclic, halogen, amino, and hydroxy; (3) Y is selected from the group consisting of H, optionally-substituted alkyl, optionally-substituted aryl, optionally-substituted cycloalkyl, optionally-substituted, heterocyclic moieties; and (4) Z is selected from the group consisting of H, optionally-substituted alkyl, optionally-substituted aryl, optionally-substituted cycloalkyl, and optionally-substituted heterocyclic moieties; and wherein: (a) Y and Z optionally bind together to form a ring; (b) R' is selected from the group consisting of H, optionally-substituted alkyl, optionally-substituted aryl, optionally-substituted cycloalkyl, and optionally-substituted heterocyclic; (c) R" is independently selected from the group consisting of H, optionally-substituted alkyl, optionally-substituted aryl, optionally-substituted cycloalkyl, and optionally-substituted heterocyclic; wherein one or more of the alkyl, cycloalkyl, heterocycloalkyl, aryl or heteroaryl moieties may be substituted by one or more $C_1$-$C_6$ alkoxy, halogen or deuterium.

In another embodiment, W is selected from the group consisting of H, optionally-substituted alkyl, and optionally-substituted aryl; wherein X is selected from the group consisting of H, optionally-substituted alkyl, and optionally-substituted aryl; and wherein W and X cannot both be H.

In another embodiment, Y is selected from the group consisting of H, optionally-substituted alkyl, and optionally-substituted aryl; wherein Z is selected from the group consisting of H, optionally-substituted alkyl, and optionally-substituted aryl; and wherein Y and Z cannot both be H.

In another embodiment, R' is H. In another embodiment, R" is H. In another embodiment, R is

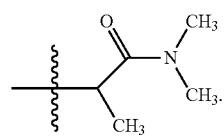

In another embodiment, R is

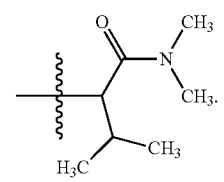

In another embodiment, R is

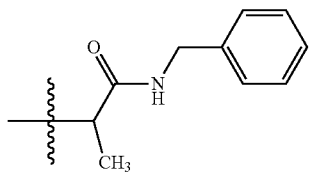

In another embodiment, R is

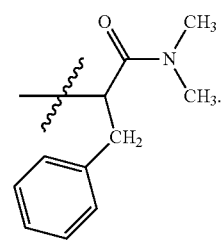 [SMILES: *C(Cc1ccccc1)C(=O)N(C)C]

Other aspects of the present invention include a pharmaceutical composition comprising a compound of any one of the prior embodiments and at least one pharmaceutically acceptable excipient.

Another aspect of the present invention includes a method of treating idiopathic pulmonary fibrosis (IPF) in a patient in need thereof comprising administering to the patient a therapeutically effective amount of a compound of any of the prior embodiments, or a pharmaceutically acceptable salt thereof, wherein the compound is capable of inhibiting TGFβ pathway and the compound binds to FIEL1.

Yet another aspect of the present invention includes methods of treating a disease associated with an activated inflammatory pathway such as the NF-kB, TGFβ and JAK/STAT pathway, comprising administering to a subject in need thereof a therapeutically effective amount of a compound of any of the prior embodiments, or a pharmaceutically acceptable salt thereof, wherein the compound is capable of inhibiting NF-kB, TGFβ and/or JAK/STAT pathways, and wherein the compound binds to FIEL1. In some embodiments, the disease associated with NF-kB, TGFβ and JAK/STAT pathway is selected from a group consisting asthma, chronic obstructive lung disease, pulmonary fibrosis, pneumonitis, pneumonia, cystic fibrosis, psoriasis, arthritis/rheumatoid arthritis, rhinitis, pharyngitis, cystitis, prostatitis, dermatitis, allergy, nephritis, conjunctivitis, encephalitis, meningitis, opthaltnitis, uveitis, pleuritis, pericarditis, myocarditis, atherosclerosis, multiple sclerosis, human immunodeficiency virus related inflammation, diabetes, osteoarthritis, psoriatic arthritis, inflammatory bowel disease, colitis, sepsis, vasculitis, bursitis, connective tissue disease, autoimmune disease, viral or influenza-induced inflammation, or edema. In some embodiments, the therapeutic effective amount of a compound of any prior embodiment is about 0.1-about 20 mg/kg/d. In some embodiments, the administration of the compound of any of the prior embodiment is via any pharmaceutically acceptable method, including but not limited to oral, inhalation, intravenous, or intramuscular.

The foregoing general description and following description of the drawings and detailed description are exemplary and explanatory and are intended to provide further explanation of the invention as claimed. Other objects, advantages, and novel features will be readily apparent to those skilled in the art from the following brief description of the drawings and detailed description of the invention.

BRIEF DESCRIPTION OF THE DRAWINGS

FIG. 1A shows Immunoblots of levels of PIAS4 proteins and V5 after KIAA0317 (823aa, AREL1) and (789aa, FIEL1) plasmid expression (n=2). FIG. 1B shows immunoprecipitation of PIAS4 protein from cell lysate using a PIAS4 antibody and coupled to protein A/G beads. PIAS4 beads were then incubated with in vitro synthesized products expressing HIS-V5-FIEL1 (789aa) or HIS-V5-AREL1 (823aa). After washing, proteins were eluted and processed for V5 immunoblotting (n=2). FIG. 1C shows an in vitro ubiquitination assay. Purified E1 and E2 components were incubated with V5-PIAS4, FIEL1, and the full complement of ubiquitination reaction components (second lane) showed polyubiquitinated PIAS4 proteins (n=3). FIGS. 1D-E. PIAS4 protein in murine lung epithelial cells (MLE) half-life determination with empty plasmid (E) or FIEL1 expression (top panel); PIAS4 protein half-life determination with CON shRNA or KIAA0317 shRNA expression (bottom panel) (n=3). FIG. 1F shows the results of treatment of MRC5 cells with TGFβ in a time or dose dependent manner; cells were collected and immunobloted for FIEL1, PIAS4, and Actin. Endogenous FIEL1 was also immunoprecipitated and immunobloted for PIAS4 (n=3). FIG. 1G shows the results of immunoblotting of PIAS4 and FIEL1 from five control and five IPF patient lungs. PIAS4 and both the shorter and longer forms of KIAA0317 were quantified using ImageJ and graphed. FIG. 1H shows the results of treatment of C57BL/6J mice with bleomycin (0.02 U) for up to 21 days. Mice were then euthanized, and lungs were isolated and assayed for PIAS4 and FIEL1 immunoblotting. Bands corresponding to each protein on immunoblots were quantified using ImageJ software, and the results are displayed graphically. n=4, *p<0.05 compared to day 0 (t-test).

FIGS. 2A& F SMAD reporter assays. 293T cells were co-transfected with Cignal SMAD dual luciferase reporter plasmids along with Empty (E), FIEL1, con shRNA, or KIAA0317 shRNA. 24 h later, cells were treated with TGFβ for 2-18 h. Cells were collected and assayed for luciferase activity to evaluate SMAD promoter activity (n=3). FIGS. 2B&G 293T cells were transfected with Empty (E), FIEL1, CON shRNA, or KIAA0317 shRNA for 48 h before TGFβ treatment (0-2 ng/ml) for 1 h. Cells were then collected and immunobloted. Cell lysates were immunoprecipitated using SUMO antibody before SMAD2, 3, and 4 immunoblotting (n=2). FIGS. 2C&H. 293T cells were transfected with Empty (E), FIEL1, CON shRNA, or KIAA0317 shRNA for 48 h before TGFβ treatment (2 ng/ml) for up to 1 h. Cells were then collected and nuclear/cytosol fractions were isolated before being immunobloted. FIGS. 2D&I. MRC5 cells were transfected with Empty (E), FIEL1, CON shRNA, or KIAA 0317 shRNA for 48 h before TGFβ dose course treatment for an additional 18 h. Cells were then collected and immunobloted (n=2). FIGS. 2E&J. MRC5 cells were seeded in 35 mm glass bottom dishes before being transfected with Empty (E), FIEL1, CON shRNA, or KIAA0317 shRNA for 48 h before TGFβ treatment for an additional 18 h. Cells were then fixed and immunostained with α-SMA and FN antibodies. The nucleus was counterstained with DAPI (n=3).

FIG. 3A. Endogenous PIAS4 was immunoprecipitated and immunoblotted for Erk1, PKCα, and PKCξ (n=2). FIG. 3B. MLE cells were transfected with increasing amounts of PKCξ or JNK1 plasmids for 18 h before PIAS4 immunoblotting (n=2). FIG. 3C. PIAS4 protein half-life determination with CON shRNA or PKCξ shRNA expression (n=3). FIG. 3D. PIAS4 protein half-life determination with Empty or PKCξ plasmid overexpression (n=3). FIGS. 3E-F. MRC5 cells were treated with TGFβ in a time or dose dependent manner; cells were collected and immunoblotted for FIEL1, PIAS4, PKCξ, p-PKCξ, and Actin. Endogenous PIAS4 was also immunoprecipitated and followed by PKCξ, PKCα, phospho-serine, and phospho-threonine immunoblotting (n=2). FIG. 3G. In vitro PKCξ kinase assay using PIAS4 as the substrate. *heat inactivated PKCξ (n=2). FIG. 3H. Immunoblots showing levels of FIEL1, PKCξ, p-PKCξ, and PIAS4 protein in 293T cells transfected with either con shRNA or PKCξ shRNA followed by a TGFβ dose treatment. Endogenous PIAS4 was also immunoprecipitated and followed by PKCξ, phospho-serine, and phospho-threonine immunoblotting. FIG. 3I. 293T cells were transfected with WT, S14A, S18A, or S14/18A PIAS4 before being treated with a dose course of TGFβ. Cells were then collected and assayed for V5-PIAS4. Overexpressed V5-PIAS4 was also immunoprecipitated using a V5 antibody and followed by phospho-serine immunoblotting (n=2). FIG. 3J. Four biotin labeled PIAS4 peptides were bound to streptavidin and served as the bait for FIEL1 binding. After washing, proteins were eluted and immunobloted for FIEL1-V5 (n=2).

FIG. 4A. Endogenous PIAS4 was immunoprecipitated and followed by JNK2, PKCα, and GSK3β antibody immunoblotting (n=2). FIG. 4B. MLE cells were transfected with increasing amounts of WT or constitutively activated GSK3β hyper mutant plasmids for 18 h before PIAS4 immunoblotting. The arrow indicates the overexpressed GSK3β (n=2). FIG. 4C. PIAS4 protein half-life determination with WT GSK3β or Hyperactive GSK3β plasmid overexpression. The arrow indicates the overexpressed GSK3β (n=2). FIG. 4D. MRC5 cells were treated with TGFβ in a time or dose dependent manner; cells were then collected and immunobloted for FIEL1, PIAS4, and Actin. Endogenous FIEL1 was also immunoprecipitated and followed by phospho-serine and phospho-threonine immunoblotting (n=2). FIG. 4E. Immunoblots showing levels of GSK3β, PIAS4, and FIEL1 protein in 293T cells transfected with either CON shRNA or GSK3β shRNA followed by a TGFβ dose treatment. Endogenous PIAS4 was also immunoprecipitated and followed by phospho-serine and phospho-threonine immunoblotting. FIG. 4F. Lung samples from FIG. 1F were subjected to FIEL1 immunoprecipitation, followed by PIAS4 and phospho-threonine immunoblotting. FIG. 4G. In vitro GSK3β kinase assay using PIAS4 as the substrate. *heat inactivated GSK3β (n=2). FIG. 4H. 293T cells were transfected with Empty, WT, or T783A FIEL1 for 24 h. Cells were then collected and immunobloted for V5-FIEL1 and PIAS4. Overexpressed V5-FIEL1 was also immunoprecipitated using V5 antibody and followed by phospho-threonine immunoblotting (n=2). FIG. 4I. Four biotin labeled FIEL1 peptides were pre-bound to streptavidin and served as the bait for PIAS4 binding. After washing, proteins were eluted and processed for PIAS4 immunoblotting (n=2). FIG. 4J. PIAS4 Peptide 2 (Biotin-MSFRVS(p)DLQM) was pre-bound to streptavidin and served as the bait for FIEL1 binding. After washing, proteins were eluted and processed for FIEL1 immunoblotting (n=2). FIG. 4K. FIEL1 Peptide 2 (Biotin-QIIAAPTHST(p)LPTA) was bound to streptavidin and served as the bait for PIAS4 binding. After washing, proteins were eluted and processed for PIAS4 immunoblotting (n=2).

FIG. 5G. Survival studies of mice that were given bleomycin. Mice were carefully monitored over time, moribund, preterminal animals were immediately euthanized and recorded as deceased. Kaplan-Meier survival curves were generated using SPSS software (p<0.05). Empty: n=9, FIEL1: n=11. FIG. 5H. Hydroxyproline contents were measured in lungs from 7, 14, and 21 d after bleomycin challenge. I. H&E and Trichrome staining was performed on lung samples. Original magnification, ×10. *p<0.05 compared to Empty (t-test). Data are an average of two experiments (A-I, 4-6 mice/group).

FIG. 6G. Survival studies of mice that were given bleomycin. Mice were carefully monitored over time; moribund, preterminal animals were immediately euthanized and recorded as deceased. Kaplan-Meier survival curves were generated using SPSS software (p<0.05). CON shRNA: n=8, KIAA0317 shRNA: n=8. FIG. 6H. Hydroxyproline contents were measured in lungs from 7, 14, and 21 d after bleomycin challenge. I. FIGS. 6H&E and Trichrome staining was performed on lung samples. Original magnification, ×10. *p<0.05 compared to Empty (t-test). Data are an average of two experiments (A-I, 4-6-mice/group).

FIGS. 7A-I shows a FIEL inhibitor binding site, and inhibition of FIEL1 and PIAS4 interaction by representative inhibitors (BE 1480 and BC 1485). FIG. 7A. Structural analysis of the FIEL1 HECT domain revealed a major cavity within the c-terminal of the HECT domain. FIG. 7B. Structures of the BC-1480 backbone and lead compound BC-1485. FIG. 7C. FIEL1 protein was HIS-purified from FIEL1 expression in 293T cells using cobalt beads. Beads were then extensively washed prior to exposure to BC-1480 or BC-1485 at different concentrations ($10^{-4}$ to 100 µM). Purified PIAS4 protein was then incubated with drug-bound FIEL1 beads overnight. Beads were washed, and proteins were eluted and resolved on SDS-PAGE. The relative amounts of PIAS4 detected in the pull-downs was normalized to loading and quantified (n=2). FIG. 7D. MLE cells were exposed to BC-1480 or BC-1485 at various concentrations for 18 h. Cells were then collected and immunoblotted. FIGS. 7E-J. C57BL/6J mice were administered with bleomycin (0.05 U) for 7-21 days. Compounds BC-1480 and BC-1485 were given to mice through drinking water with an estimated dose of 5 mg/kg/d. Mice were euthanized, and lungs were lavaged with saline, harvested, and then homogenized. Lavage proteins, CXCL1, and total cell count were measured in FIGS. 7E-G. H. Survival studies of mice that were given bleomycin and compound treatments. Mice were carefully monitored over time; moribund, preterminal animals were immediately euthanized and recorded as deceased. Kaplan-Meier survival curves were generated using SPSS software (p<0.01 compared to Vehicle). Vehicle: n=24, BC-1480: n=13, BC-1485: n=12. FIG. 7I. Hydroxyproline contents were measured in lungs from 7, 14, and 21 d after bleomycin challenge. FIG. 7J. Trichrome staining was performed on lung samples from E. Original magnification, ×10. *p<0.05 compared to Vehicle (t-test). Data are an average of two experiments (FIGS. 7E-J, 4-8 mice/group)

FIG. 9A. PIAS4 protein half-life study in MLE cells transfected with Empty plasmid or Ubiquitin plasmid. FIG. 9B. PIAS4 protein half-life study with MG132 or Leupeptin. FIG. 9C. Immunoblots showing levels of PIAS4 proteins and V5 after ectopic FIEL1 or UBE3B plasmid expression. FIG. 9D. Immunoblots showing levels of FIEL1 proteins after ectopic FIEL1 plasmid expression in MLE, HeLa, and 293T cells. FIG. 9E. Immunoblots showing levels of PIAS4 proteins and V5 after ectopic FIEL1 plasmid expression in HeLa and 293T cells. FIG. 9F. MLE cells were transfected with an inducible control or FIEL1 plasmid under control of exogenous doxycycline. Cells were treated with doxycycline in a dose dependent manner. Cells were then collected and cell lysates were immunoblotted for FIEL1 and PIAS4. FIG. 9G. MRC5 cells were exposed to TGFβ for 24 h before being assayed for PIAS4 and FIEL1 protein half-lives.

FIG. 10A. Several point mutants of PIAS4 were designed and cloned into a pcDNA3.1D/V5-HIS vector. FIG. 10B. Half-life study of WT, K31R, K35R, and K114R PIAS4 in MLE cells. C. MLE cells were co-transfected with WT or PIAS4 lysine mutants with or without HA-Ubiquitin. Cells were then collected and immunobloted. PIAS4 protein levels were quantified and graphed n=3.

FIG. 11A. Several deletional mutants of PIAS4 were designed and cloned into a pcDNA3.1D/V5-HIS vector. FIGS. 11B-C. FIEL1 protein was immunoprecipitated from cell lysates using a KIAA0317 antibody and coupled to protein A/G beads. FIEL1 beads were then incubated with in vitro synthesized products expressing HIS-V5-PIAS4 mutants. After washing, proteins were eluted and processed for V5-PIAS4 immunoblotting. FIG. 11D. Half-life study of WT, Q21A, S14A, S18A, S18A/Q21A, and S14A/S18A PIAS4 in MLE cells. FIG. 11E. MLE cells were co-transfected with WT or PIAS4 mutants with or without FIEL1. Cells were then collected and immunobloted.

FIG. 12A. Several deletional mutants of FIEL1 were designed and cloned into a pcDNA3.1D/V5-HIS vector. FIGS. 12B-F, H. PIAS4 protein was immunoprecipitated from cell lysate using a PIAS4 antibody and coupled to protein A/G beads. PIAS4 beads were then incubated with in vitro synthesized products expressing HIS-V5-FIEL1 mutants. After washing, proteins were eluted and processed for V5-FIEL1 immunoblotting. FIG. 12G. MLE cells were transfected with WT or FIEL1 mutants. Cells were then collected and immunoblotted for PIAS4 protein.

FIG. 13A. PIAS4 protein half-life determination with CON shRNA or GSK3β shRNA expression. FIG. 13B. MLE cells were transfected with increasing amounts of WT, T783A, or T783D mutant FIEL1 plasmids for 18 h before PIAS4 immunoblotting. FIG. 13C. PIAS4 protein half-life determination with WT, T783A, or T783D mutant FIEL1. FIG. 13D. MLE cells were transfected with increasing amounts of WT, T783A, P779L, or T783A/P779L double mutant FIEL1 plasmids for 18 h before PIAS4 immunoblotting. FIG. 13E. PIAS4 protein half-life determination with WT, T783A, P779L, or T783A/P779L double mutant FIEL1. FIG. 13F. 293T cells were transfected with WT, T783A, P779L, or T783A/P779L double mutant FIEL1 before being treated with TGFβ. Cells were then collected and assayed for PIAS4. FIG. 13G. MLE cells were transfected with increasing amounts of WT, I514V or D207V mutant FIEL1 plasmids for 18 h before PIAS4 immunoblotting. FIG. 13H. PIAS4 protein half-life determination with WT, I514V, or D207V mutant FIEL1 expression.

FIG. 15A. Diagram of the BC-1485 synthesis process. FIGS. 15B-C. Docking studies of the lead compound, BC-1485, interacting with the FIEL1-HECT domain. FIG. 15D. MRC5 cells were treated with the compound at various doses; cells were also co-treated with TGFβ at 2 ng/ml. 18 h later, cells were collected and assayed for α-SMA expression. FIG. 15E. MRC5 cells were seeded in 35 mm glass bottom dishes before co-treatment with TGFβ at 2 ng/ml and BC-1480 or BC1485 at 5 µM. FIG. 15F. PIAS4 protein half-life determination after BC-1480 or BC1485 treatment at 5 µM for 18 h. FIG. 15G, PIAS4 and KIAA0317 mRNA analysis after BC1485 treatment for 18 h.

FIG. 17E. H&E staining was performed on lung samples from FIG. 17A (Original magnification, ×10). Data are an average of two experiments (A-E, n=5-10 mice/group).

FIG. 18E. H&E staining was performed on lung samples from FIG. 18A (Original magnification, ×20) A-E, n=4 mice/group.

FIG. 20G provides pictures of the tissues at interest.

DETAIL DESCRIPTION

I. Compounds

Compounds of the present disclosure include novel compounds represented by Formula (I):

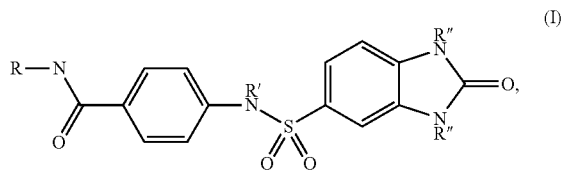

Wherein R is:

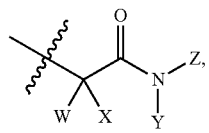

and wherein:
(1) W is selected from the group consisting of H, optionally-substituted alkyl, optionally-substituted alkoxy, optionally-substituted aryl, optionally-substituted cycloalkyl, optionally-substituted heterocyclic, halogen, amino, and hydroxy;
(2) X is selected from the group consisting of H, optionally-substituted alkyl, optionally-substituted alkoxy, optionally-substituted aryl, optionally-substituted cycloalkyl, optionally-substituted heterocyclic, halogen, amino, and hydroxy;
(3) Y is selected from the group consisting of H, optionally-substituted alkyl, optionally-substituted aryl, optionally-substituted cycloalkyl, optionally-substituted heterocyclic moieties;
(4) Z is selected from the group consisting of H, optionally-substituted alkyl, optionally-substituted aryl, optionally-substituted cycloalkyl, and optionally-substituted heterocyclic moieties;
and wherein Y and Z optionally bind together to form a ring;
(5) R' is selected from the group consisting of H, optionally-substituted alkyl, optionally-substituted aryl, optionally-substituted cycloalkyl, and optionally-substituted heterocyclic;
(6) R" is independently selected from the group consisting of H, optionally-substituted alkyl, optionally-substituted aryl, optionally-substituted cycloalkyl, and optionally-substituted heterocyclic;

wherein one or more of the alkyl, cycloalkyl, heterocycloalkyl, aryl or heteroaryl moieties may be substituted by one or more $C_1$-$C_6$ alkoxy, halogen or deuterium.

In another embodiment, W is selected from the group consisting of H, optionally-substituted alkyl, and optionally-substituted aryl; wherein X is selected from the group consisting of H, optionally-substituted alkyl, and optionally-substituted aryl; and wherein W and X cannot both be H. In some embodiments, W is selected from the group consisting of H and $C_1$-$C_6$ alkyl.

In another embodiment, Y is selected from the group consisting of H, optionally-substituted alkyl, and optionally-substituted aryl; wherein Z is selected from the group consisting of H, optionally-substituted alkyl, and optionally-substituted aryl; and wherein Y and Z cannot both be H. In some embodiments, X is selected from the group consisting of H, $C_1$-$C_6$ alkyl, and $(C_0$-$C_6)$alkyl$(C_6$-$C_{12})$aryl.

In another embodiment, R' is H or R' is selected from the group consisting of H and $C_1$-$C_6$ alkyl, and R" is selected from the group consisting of H and $C_1$-$C_6$ alkyl. In another embodiment, R" is H. In another embodiment, R is

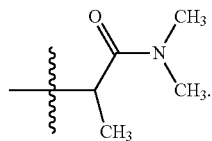

In another embodiment, R is

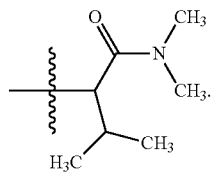 [SMILES: *C(C(=O)N(C)C)C(C)C]

In another embodiment, R is

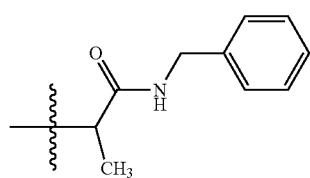

In another embodiment, R is

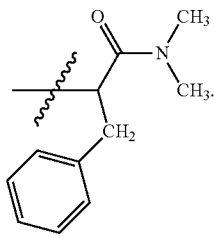 [SMILES: *C(Cc1ccccc1)C(=O)N(C)C]

Figure 14:
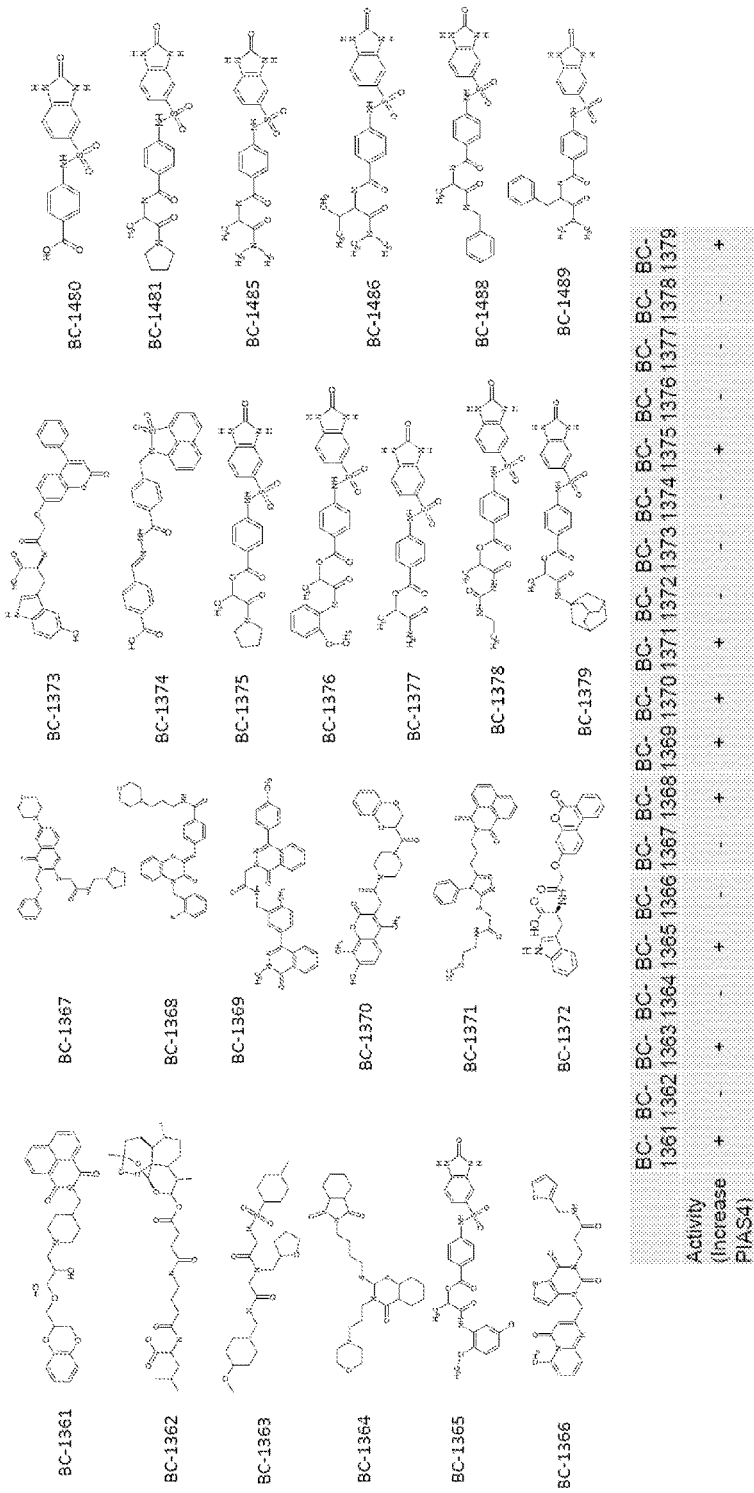
FIG. 14 shows representative inhibitors of FIEL1.

Specific embodiments of compounds of the present invention include the compounds in FIG. 14. Additional embodiments are indicated in Table 1, below.

TABLE 1

[Structure: Z-N(Y)-C(W)(X)-C(=O)-NH-phenyl-N(R')-S(=O)₂-benzimidazolone(R",R")(=O)]

| R' | R" | W | X | Y | Z |
|---|---|---|---|---|---|
| H | H | H | C₁–C₆ alkyl | H | benzyl (phenyl-CH₂) |
| C₁–C₆ alkyl | H | H | C₁–C₆ alkyl | H | benzyl (phenyl-CH₂) |
| H | H | H | C₁–C₆ alkyl | C₁–C₆ alkyl | C₁–C₆ alkyl |
| C₁–C₆ alkyl | H | H | C₁–C₆ alkyl | C₁–C₆ alkyl | C₁–C₆ alkyl |
| H | H | H | C₁–C₆ alkyl | | |
| C₁–C₆ alkyl | H | H | C₁–C₆ alkyl | | pyrrolidinyl (N-linked) |
| H | H | H | C₁–C₆ alkyl | | pyrrolidinyl (N-linked) |
| H | H | H | C₁–C₆ alkyl | | pyrrolidinyl (C-linked) |
| H | H | H | benzyl | H | C₁–C₆ alkyl |
| H | H | H | benzyl | C₁–C₆ alkyl | C₁–C₆ alkyl |
| H | H | H | C₁–C₆ alkyl | H | adamantyl |
| H | H | H | C₁–C₆ alkyl | H | phenyl |
| H | H | H | C₁–C₆ alkyl | H | indolyl |

Other embodiments include one or more of the embodiments in Table 1, wherein one of the defined moieties is substituted by alkoxy, halogen, amino, or hydroxy. In another embodiment, when the X, Y, Z moiety contains a phenyl moiety it may be substituted by one or more of alkoxy, halogen, amino, or hydroxy. In another embodiment, one or more of the moieties in Table 1 is substituted by a C₁-C₆ alkoxy, halogen or deuterium.

II. Methods of Treatment

One aspect of the present technology includes methods of treating idiopathic pulmonary fibrosis (IPF) in a patient in need thereof comprising administering to the patient a therapeutically effective amount of a compound, or a pharmaceutically acceptable salt thereof, wherein the compound is capable of inhibiting TGFβ pathway, and wherein the compound binds to FIEL1.

In some embodiments, the compound, or a pharmaceutically acceptable salt thereof, capable of inhibiting TGFβ pathway, and binding to FIEL1 is represented by Formula (I) or is represented by any other embodiment disclosed in the section titled "Compounds of the invention."

The subject being treated may be a mammal, for example, in a preferred embodiment the subject is a human.

Another aspect of the present technology includes methods of treating a disease associated with an activated inflammatory pathway such as NF-kB, TGFβ and JAK/STAT pathway comprising administering to a subject in need thereof a therapeutically effective amount of a compound, or a pharmaceutically acceptable salt thereof, wherein the compound is capable of inhibiting NF-kB, TGFβ and/or JAK/STAT pathways, and wherein the compound binds to FIEL1, and wherein the compound is represented by Formula (I). In one embodiment the subject is a human.

Another aspect of the present technology includes methods of treating a disease associated with an activated inflammatory pathway such as NF-kB, TGFβ and JAK/STAT pathway, wherein the disease associated with the activated inflammatory pathway such as NF-kB, TGFβ and JAK/STAT pathway is selected from the group consisting of asthma, chronic obstructive lung disease, pulmonary fibrosis, pneumonitis, pneumonia, cystic fibrosis, psoriasis, arthritis/rheumatoid arthritis, rhinitis, pharyngitis, cystitis, prostatitis, dermatitis, allergy, nephritis, conjunctivitis, encephalitis, meningitis, opthahnitis, uveitis, pleuritis, pericarditis, myocarditis, atherosclerosis, multiple sclerosis, human immunodeficiency virus related inflammation, diabetes, osteoarthritis, psoriatic arthritis, inflammatory bowel disease, colitis, sepsis, vasculitis, bursitis, connective tissue disease, autoimmune disease, viral or influenza-induced inflammation, or edema.

Compounds represented by Formula 1, or pharmaceutically acceptable salts or solvates thereof, or a composition comprising such a compound or a pharmaceutically acceptable salt or solvate thereof, can be administered to a patient or subject in need of treatment either individually, or in combination with other therapeutic agents that have similar or synergistic biological activities. Additionally, Formula I compounds and compositions can be administered as a single dose or as multiple daily doses by a practicing medical practitioner.

A composition comprising a compound of the present disclosure may be administered to individuals in a formulation with one or more pharmaceutically acceptable excipient(s). Wide varieties of pharmaceutically acceptable excipients are known in the art and need not be discussed in detail herein. Pharmaceutically acceptable excipients have been amply described in a variety of publications, including, for example, A. Gennaro (2000) "Remington: The Science and Practice of Pharmacy", 20th edition, Lippincott, Williams, & Wilkins; Pharmaceutical Dosage Forms and Drug Delivery Systems (1999) H. C. Ansel et al., eds 7th ed., Lippincott, Williams, & Wilkins; and Handbook of Pharmaceutical Excipients (2000) A. H. Kibbe et al., eds., 3rd ed. Amer. Pharmaceutical Assoc.

In the subject methods, the active agent(s) may be administered to the host using any convenient means capable of resulting in the desired therapeutic effect. Thus, the agent can be incorporated into a variety of formulations for therapeutic administration. More particularly, the agents of the present invention can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, solutions, suppositories, injections, inhalants and aerosols. As such, administration of the agents can be achieved in various ways, including but not limited to oral, buccal, rectal, parenteral, intraperitoneal, intradermal, topical, pulmonary, nasal, inhalation, transdermal, intracheal, etc., administration.

The dosage administered will be dependent upon multiple factors, such as the age, health, weight, and/or disease state of the recipient, kind of concurrent treatment, if any, frequency of treatment, and/or the nature and magnitude of the biological effect desired. An exemplary dosage may be about 0.1-about 20 mg/kg/d, or any amount inbetween these two amounts. Other exemplary dosages include, but are not limited to, about 0.1 about 10 mg/kg/d or about 0.5-about 10 mg/kg/d. Still other exemplary dosages include, but are not limited to, about 0.1, about 0.2, about 0.3, about 0.4, about 0.5, about 0.6, about 0.7, about 0.8, about 0.9, about 1, about 1.5, about 2, about 2.5, about 3, about 3.5, about 4, about 4.5, about 5, about 5.5, about 6, about 6.5, about 7, about 7.5, about 8, about 8.5, about 9, about 9.5, about 10, about 10.5, about 11, about 11.5, about 12, about 12.5, about 13, about 13.5, about 14, about 14.5, about 15, about 15.5, about 16, about 16.5, about 17, about 17.5, about 18, about 18.5, about 19, about 19.5, or about 20 mg/kg/d. When combination therapy is used, the compound and the other therapeutic agent can be administered separately at different time intervals, or simultaneously.

III. Pharmaceutical Formulations

Pharmaceutical compositions and medicaments may be prepared by mixing one or more compounds of the invention, prodrugs thereof, pharmaceutically acceptable salts or solvates thereof, stereoisomers thereof, tautomers thereof, or solvates thereof, with pharmaceutically acceptable carriers, excipients, binders, diluents or the like to treat idiopathic pulmonary fibrosis (IPF) or a disease associated with activated inflammatory pathway such as NF-kB, TGFβ and JAK/STAT pathway.

In the subject methods, the active agent(s) may be administered to the host using any convenient means capable of resulting in the desired therapeutic effect Thus, the agent can be incorporated into a variety of formulations for therapeutic administration. More particularly, the agents of the present invention can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, solutions, suppositories, injections, inhalants and aerosols.

In pharmaceutical dosage forms, the agents may be administered in the form of their pharmaceutically acceptable salts, or they may also be used alone or in appropriate association, as well as in combination, with other pharmaceutically active compounds. The following methods and excipients are merely exemplary and are in no way limiting.

The compounds and compositions of the invention may be used to prepare formulations and medicaments that prevent or treat idiopathic pulmonary fibrosis (IPF), as described herein. Other diseases or disorders can be treated include inflammatory disorders such as asthma, chronic obstructive lung disease, pulmonary fibrosis, pneumonitis, pneumonia, cystic fibrosis, psoriasis, arthritis/rheumatoid arthritis, rhinitis, pharyngitis, cystitis, prostatitis, dermatitis, allergy, nephritis, conjunctivitis, encephalitis, meningitis, opthalmitis, uveitis, pleuritis, pericarditis, myocarditis, atherosclerosis, multiple sclerosis, human immunodeficiency virus related inflammation, diabetes, osteoarthritis, psoriatic arthritis, inflammatory bowel disease, colitis, sepsis, vasculitis, bursitis, connective tissue disease, autoimmune disease, viral or influenza-induced inflammation, or edema.

Such compositions can be in any pharmaceutically acceptable form, such as but not limited to in the form of, for example, granules, powders, tablets, capsules, syrup, suppositories, injections, emulsions, elixirs, suspensions or solutions. The compositions can be formulated for any pharmaceutically acceptable route of administration, such as for example, by oral, parenteral, pulmonary, topical, rectal, nasal, vaginal administration, or via implanted reservoir. Parenteral or systemic administration includes, but is not limited to, subcutaneous, intravenous, intraperitoneally, intramuscular, intra-articular, intrasynovial, intrasternal, intrathecal, intralesional and intracranial injections. The following dosage forms are given by way of example and should not be construed as limiting the invention.

Pharmaceutically acceptable salts of the invention compounds are considered within the scope of the present invention. The compounds of the invention have a number of basic nitrogen groups, and as such, pharmaceutically acceptable salts can be formed with inorganic acids (such as hydrochloric acid, hydroboric acid, nitric acid, sulfuric acid, and phosphoric acid), organic acids (e.g. formic acid, acetic acid, trifluoroacetic acid, fumaric acid, oxalic acid, tartaric acid, lactic acid, maleic acid, citric acid, succinic acid, malic acid, methanesulfonic acid, benzenesulfonic acid, and p-toluenesulfonic acid) or acidic amino acids (such as aspartic acid and glutamic acid). The compounds of the present invention may have acidic substituent groups, and in such cases, it can form salts with metals, such as alkali and earth alkali metals (e.g. $Na^+$, $Li^+$, $K^+$, $Ca^{2+}$, $Mg^{2+}$, $Zn^{2+}$), organic amines (e.g. ammonia, trimethylamine, triethylamine, pyridine, picoline, ethanolamine, diethanolamine, triethanolamine) or basic amino acids (e.g. arginine, lysine and ornithine).

Certain compounds within the scope of the invention are derivatives referred to as prodrugs. The expression "prodrug" denotes a derivative of a known direct acting drug, e.g. esters and amides, which derivative has enhanced delivery characteristics and therapeutic value as compared to the drug, and is transformed into the active drug by an enzymatic or chemical process; see Notari, R. E., "Theory and Practice of Prodrug Kinetics," *Methods in Enzymology*, 112: 309-23 (1985); Bodor, N., "Novel Approaches in Prodrug Design," *Drugs of the Future*, 6: 165-82 (1981); and Bundgaard, H., "Design of Prodrugs: Bioreversible-Derivatives for Various Functional Groups and Chemical Entities," in DESIGN OF PRODRUGS (H. Bundgaard, ed.), Elsevier (1985), and Goodman and Gilmans, *The Pharmacological Basis Of Therapeutics*, 8th ed., McGraw-Hill (1992).

For oral, buccal, and sublingual administration, powders, suspensions, granules, tablets, pills, capsules, gelcaps, and caplets are acceptable as solid dosage forms. These can be prepared, for example, by mixing one or more compounds of the present invention, or pharmaceutically acceptable salts or tautomers thereof, with at least one additive such as a starch or other additive. Suitable additives include any pharmaceutically acceptable excipient, including but not limited to sucrose, lactose, cellulose sugar, mannitol, maltitol, dextran, starch, agar, alginates, chitins, chitosans, pectins, tragacanth gum, gum arabic, gelatins, collagens, casein, albumin, synthetic or semi-synthetic polymers or glycerides. Optionally, oral dosage forms can comprise other ingredients to aid in administration, such as an inactive diluent, or lubricants such as magnesium stearate, or preservatives such as paraben or sorbic acid, or anti-oxidants such as ascorbic acid, tocopherol or cysteine, a disintegrating agent, binders, thickeners, buffers, sweeteners, flavoring agents or perfuming agents. Tablets and pills may be further treated with suitable coating materials known in the art.

IV. Definitions

As used herein and in the appended claims, the singular forms "a", "an", and "the" include plural referents unless the context clearly dictates otherwise. The claims may be drafted to exclude any optional element. As such, this statement is intended to serve as antecedent basis for use of such exclusive terminology as "solely", "only" and the like in connection with the recitation of claim elements, or use of a "negative" limitation.

As used herein, the term "about" will be understood by persons of ordinary skill in the art and will vary to some extent depending upon the context in which it is used. If there are uses of the term which are not clear to persons of ordinary skill in the art given the context in which it is used, "about" will mean up to plus or minus 10% of the particular term.

By "pharmaceutically acceptable" is meant a material that is not biologically or otherwise undesirable, i.e., the material may be incorporated into a pharmaceutical composition administered to a patient without causing any undesirable biological effects or interacting in a deleterious manner with any of the other components of the composition in which it is contained. When the term "pharmaceutically acceptable" is used to refer to a pharmaceutical carrier or excipient, it is implied that the carrier or excipient has met the required standards of toxicological and manufacturing testing or that it is included on the Inactive Ingredient Guide prepared by the U.S. and Drug administration.

By "patient" is meant any animal for which treatment is desirable. Patients may be mammals, and typically, as used herein, a patient is a human individual.

The term "pharmaceutically acceptable salt," as used herein, represents salts or zwitterionic forms of the compounds of the present invention which are water or oil-soluble or dispersible; which are suitable for treatment of diseases without undue toxicity, irritation, and allergic-response; which are commensurate with a reasonable benefit/risk ratio; and which are effective for their intended use. The salts can be prepared during the final isolation and purification of the compounds or separately by reacting the appropriate compound in the form of the free base with a suitable acid. Representative acid addition salts include acetate, adipate, alginate, L-ascorbate, aspartate, benzoate, benzenesulfonate (besylate), bisulfate, butyrate, camphorate, camphorsulfonate, citrate, digluconate, formate, fumarate, gentisate, glutarate, glycerophosphate, glycolate, hemisuifate, heptanoate, hexanoate, hippurate, hydrochloride, hydrobromide, hydroiodide, 2-hydroxyethansulfonate (isethionate), lactate, maleate, malonate, DL-mandelate, mesitylenesulfonate, methanesulfonate, naphthylenesulfonate, nicotinate, 2-naphthalenesulfonate, oxalate, pamoate, pectinate, persulfate, 3-phenylproprionate, phosphonate, picrate, pivalate, propionate, pyroglutamate, succinate, sulfonate, tartrate, L-tartrate, trichloroacetate, trifluoroacetate, phosphate, glutamate, bicarbonate, para-toluenesulfonate (p-tosylate), and undecanoate. Also, basic groups in the compounds of the present invention can be quaternized with methyl, ethyl, propyl, and butyl chlorides, bromides, and iodides; dimethyl, diethyl, dibutyl, and diamyl sulfates; decyl, lauryl, myristyl, and steryl chlorides, bromides, and iodides; and benzyl and phenethyl bromides. Examples of acids which can be employed to form pharmaceutically acceptable addition salts include inorganic acids such as hydrochloric, hydrobromic, sulfuric, and phosphoric, and organic acids such as oxalic, maleic, succinic, and citric. Salts can also be formed by coordination of the compounds with an alkali metal or alkaline earth ion. Hence, the present invention contemplates sodium, potassium, magnesium, and calcium salts of the compounds of the compounds of the present invention and the like.

An "effective" amount of an agent is meant to mean an amount of a therapeutic agent, or a rate of delivery of a therapeutic agent, effective to facilitate a desired therapeutic effect. The precise desired therapeutic effect will vary according to the condition to be treated, the formulation to be administered, and a variety of other factors that are appreciated by those of ordinary skill in the art.

The term "solvates" is used in its broadest sense. For example, the term solvates includes hydrates formed when a compound of the present invention contains one or more bound water molecules.

As used herein, the term "alkyl" is used in its broadest sense. Alkyl groups may be optionally substituted as defined herein. Examples of alkyl radicals include methyl, ethyl, n-propyl, isopropyl, cyclopropyl, cyclopmpylmethyl, n-butyl, isobutyl, sec-butyl, tert-butyl, cyclobutyl, pentyl, neopentyl, iso-amyl, hexyl, cyclohexyl, trans-1,2-di-ethylcyclohexyl, octyl, nonyl and the like. For example, the abbreviation "$(C_1-C_6)$-alkyl groups" includes (C3-C6)-cycloalkyl groups as well as straight and branched alkyl groups, and "$O(C_1-C_8)$-alkyl groups" includes the straight-chain O(C1-C8)-alkyl groups, branched O(C1-C6")-alkyl groups, and cyclic O(C1-C6)-alkyl groups.

The term "alkoxy," as used herein, refers to an alkyl ether radical, wherein the term alkyl is as defined herein. Examples of suitable alkyl ether radicals include methoxy, ethoxy, n-propoxy, isopropoxy, n-butoxy, iso-butoxy, sec-butoxy, tert-butoxy, cyclopentoxy, and the like.

The term "aryl," as used herein, means a carbocyclic aromatic system containing one, two or three rings wherein such rings may be attached together in a pendent manner or may be fused. The term "aryl" embraces aromatic radicals such as phenyl, naphthyl, anthracenyl, phenanthryl, and biphenyl. The aryl groups of the present invention can be optionally substituted with one, two, three, four, or five substituents independently selected from the groups as defined herein.

The term "cycloalkyl," as used herein, refers to a saturated or partially saturated monocyclic, bicyclic or tricyclic alkyl radical wherein each cyclic moiety contains from 3 to 12, preferably three to seven, carbon atom ring members. Examples of such cycloalkyl radicals include cyclopropyl, cyclobutyl, cyclopentyl, cyclohexyl, cycloheptyl, octahydronaphthyl, 2,3-dihydro-1H-indenyl, adamantyl and the like.

The terms "heterocyclic" and, interchangeably, "heterocyclyl," as used herein, each refer to a saturated, partially unsaturated, or fully unsaturated monocyclic, bicyclic, or tricyclic heterocyclic radical containing one or more heteroatoms as ring members, wherein each said heteroatom may be independently selected from the group consisting of nitrogen, oxygen, and sulfur, and wherein there are typically 3 to 8 ring members in each ring. Most commonly heterocyclic rings contain 5 to 6 ring members. In some embodiments of this invention heterocyclic rings contain 1 to 4 heteroatoms; in other embodiments, heterocyclic rings contain 1 to 2 heteroatoms. In some embodiments, heterocyclic rings contain heteroatoms independently selected from the group consisting of nitrogen, oxygen, and sulfur or nitrogen and oxygen, or nitrogen, or oxygen.

The term "halo," or "halogen," as used herein, refers to fluorine, chlorine, bromine, or iodine. In some embodiments, the halogen may be selected from fluorine, chlorine, or bromine, individually fluorine or chlorine or bromine.

The term "amino," as used herein, refers to —NRR', wherein R and R' are independently selected from the group consisting of hydrogen, alkenyl, alkoxy, alkoxyalkyl, alkoxycarbonyl, alkyl, alkylcarbonyl, aryl, arylalkenyl, arylalkyl, cycloalkyl, haloalkylcarbonyl, heteroaryl.

The terms "hydroxy" and "hydroxyl," as used herein, refer to the —OH group.

Certain ranges are presented herein with numerical values being preceded by the term "about". The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

This invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

EXAMPLES

The present technology is further illustrated by the following examples, which should not be construed as limiting in any way.

Materials and methods: Sources of the murine lung epithelial (MLE) and 293T cells lines are described in Ray et al., *Nat. Med.*, 16(10): 1120-1127 (2010), and Chen et al., *J. of Biol. Chem.*, 282(46):33494-33506 (2007). MRC5 cells were from ATCC. Purified ubiquitin, E1, E2, MG132, Leupeptin, and cycloheximide (CHX) were purchased from Calbiochem. Mouse monoclonal V5 antibody, the pcDNA3.1D cloning kit, *E. coli* Top10 One Shot competent cells, the pENTR Directional TOPO cloning kits, and Gateway mammalian expression system were from Invitrogen. The HECT domain E3 ligase cDNA, scramble shRNA, KIAA0317, PKCξ, and GSK3β shRNA sets were purchased from OpenBiosystems. Nucleofector transfection kits were from Amaxa. Lentiviral packaging system and Cobalt beads were from Clontech. Immobilized protein A/G beads were from Pierce. In vitro transcription and translation (TnT) kits were from Promega. Cignal SMAD Reporter luciferase Kit (CCS-017L) and mRNA isolation kit were from Qiagen. Complete proteasome inhibitors were from Roche. KIAA0317 antibodies were from Aviva and Santa Cruz. PIAS and GSK3β antibodies were from Cell Signaling and Santa Cruz. CXCL1 and IL6 mouse ELISA kit and TGFβ protein were from R&D Systems. Peptides were custom synthesized from CHI Scientific. DNA sequencing was performed at Genewiz. All small molecule compound analysis was performed by the University of Pittsburgh Mass Spectrometry and NMR facility.

Human Samples: This study was approved by the University of Pittsburgh Institutional Review Board. Lung tissues were from the University of Pittsburgh lung transplant tissue bank.

Cell culture: MLE cells were cultured in Dulbecco's Modified Eagle Medium-F12 (Gibco) supplemented with 10% fetal bovine serum (DMEM-10). 293T cells were cultured in Dulbecco's Modified Eagle Medium (Gibco) supplemented with 10% fetal bovine serum (DMEM-10). MRC5 cells were cultured in Eagle's Minimum Essential Medium (Gibco) supplemented with 10% fetal bovine serum (EMEM-10). For protein expression in MLE cells, nucleofection was used following Amaxa's protocol. For protein overexpression in 293T cells, Fugene6HD transfection reagents were used following the manufacturer's protocol. For protein expression in MRC5 cells, MRC-5 Cell Avalanche™ Transfection Reagent was used following manufacturer's protocol. Cells were treated with TGFβ at 0-2 ng/ml for 0-18 h. For FIEL1, PKCξ, or GSK3β knockdown studies in cells, scramble shRNA, KIAA0317, PKCξ, or GSK3β shRNA were used to transfect cells for 48 h. For drug treatment, compounds were solubilized in DMSO before being added to the cells for up to 18 h. Cell lysates were prepared by brief sonication in 150 mM NaCl, 50 mM Tris, 1.0 mM EDTA, 2 mM dithiothreitol, 0.025% sodium azide, and 1 mM phenylmethylsulfonyl fluoride (Buffer A) at 4° C. For half-life study, MLE cells were exposed to cycloheximide (40 μg/ml) in a time dependent manner for up to 8 h. Cells were then collected and immunoblotted.

Methods

In vitro protein binding assays: PIAS4 protein was immunoprecipitated from 1 mg cell lysate using PIAS4 antibody (goat) and coupled to protein A/G agarose resin. PIAS4 beads were then incubated with in vitro synthesized products (50 ul) expressing V5-FIEL1 mutants. After washing, the proteins were eluted and processed for V5-FIEL1 immunoblotting. Similarly, FIEL1 was immunoprecipitated from 1 mg cell lysate using FIEL1 antibody (rabbit) and coupled to protein A/G agarose resin. FIEL1 beads were then incubated with in vitro synthesized products (50 ul) expressing V5-PIAS4 mutants. After washing, the proteins were eluted and processed for V5-PIAS4 immunoblotting.

In vitro peptide binding assays: Biotin labeled peptides were first coupled to streptavidin agarose beads for 1 h. Beads were then incubated with in vitro synthesized FIEL1 or PIAS4 for 18 h. After washing, proteins were eluted and processed for FIEL1 or PIAS4 immunoblotting.

In vitro drug binding assays: FIEL1 protein was HIS-purified from FIEL1 expression 293T cells using cobalt beads. Beads were then extensively washed prior to exposure to BC-1480 or BC-1485 at different concentrations ($10^{-4}$ to 100 μM). Purified recombinant PIAS4 protein was then incubated with drug-bound FIEL1 beads overnight. Beads were washed, and proteins were eluted and resolved on SDS-PAGE. The relative amounts of PIAS4 detected in the pull-downs were normalized to loading and quantified.

In vitro ubiquitin conjugation assays: The assay was performed in a volume of 25 μl containing 50 mM Tris pH 7.6, 5 mM $MgCl_2$, 0.6 mM DTT, 2 mM ATP, 1.5 ng/μl E1, 10 ng/μl $Ubc5$, 10 ng/μl Ubc7, 1 μg/μl ubiquitin (Calbiochem), 1 μM ubiquitin aldehyde, and in vitro synthesized V5-PIAS4 and FIEL1. Reaction products were processed for V5 immunoblotting.

In vitro kinase assays: The assay was performed in a volume of 25 μl containing 50 mM Tris pH 7.6, 100 mM $MgCl_2$, 0.5 mM ATP, 25 mM β-Glycerolphosphate, 0.2 μCi γ-32P ATP (Perkin-Elmer), 5 mg/mL BSA, either 500 nM of PKCζ or 500 nM of GSK3β and in vitro synthesized V5-PIAS4 and V5-FIEL1. Reaction products were processed for autoradiography using Personal Molecular Imager™ (BioRad).

Hydroxyproline Assay: Murine lungs were dried and weighed prior to digestion with HCl. Hydroxyproline concentrations were measuring using methods previously described in Kesava Reddy et al., *Clinical Biochemistry*, 29(3): 225-229 (1996), and Neuman et al., *J. of Biol. Chem.*, 184(1): 299-306 (1950). Hydroxyproline content was normalized to dry lung weight.

SMAD reporter assay: Cignal SMAD Reporter luciferase plasmids were co-transfected with Empty, FIEL1, PIAS4, CON shRNA, or KIAA0317 shRNA for 24-48 h before TGFβ treatment for an additional 2-18 h. Cells were then collected and assayed for firefly and renilla luciferase activity. SMAD transcription activity was normalized by a firefly and renilla luciferase activity ratio.

Immunostaining: MRC5 cells were seeded in 35 mm MatTek glassbottom dishes before the plasmid transfection, inhibitor and TGFβ treatment. Cells were washed with PBS and fixed with 4% paraformaldehyde for 20 min, then exposed to 2% BSA, 1:500 mouse α-SMA and goat FN antibodies, and 1:1000 Alexa 488 or Alexa 567 labeled chicken anti-mouse or donkey anti-goat secondary antibodies sequentially for immunostaining. Nucleus was counterstained with DAPI. Immunofluorescent cell imaging was performed on a Nikon A1 confocal microscope using 405 nm, 488 nm or 567 nm wavelengths. All experiments were done with a 60× oil differential interference contrast objective lens.

Molecular docking studies and compound design: The docking experiments were carried out using software from Discovery Studio 3.5. A library containing 500K approved or experimental drugs was first used to screen potential ligands for FIEL1. FIEL1-HECT domain structural analysis revealed a major drug binding cavity within the c-terminal of the HECT domain. The binding cavity was adopted into the LibDock algorithm to screen for the optimum inhibitor. Based on the docking and best-fit analysis of suitable ligands, BC-1480 was used as the backbone to synthesize other compounds.

RT-qPCR, cloning, and mutagenesis: Total RNA was isolated and reverse transcription was performed followed by real-time quantitative PCR with SYBR Green qPCR mixture as described in Butler et al. *J. Biol. Chem.* 2010, 185(9): 6246-6258. All mutant PIAS4 and KIAA0317 plasmid constructs were generated using PCR-based approaches and appropriate primers and subcloned into a pcDNA3.1D/V5-HIS vector.

Lentivirus construction: To generate lentivirus encoding FIEL1, Lenti-Plvx-FIEL1 plasmid was co-transfected with Lenti-X HTX packaging plasmids (Clontech) into 293T cells following the manufacturer's instructions. 72 h later, virus was collected and concentrated using Lenti-X concentrator.

Animal studies: All procedures were approved by the University of Pittsburgh Institutional Animal Care and Use Committee. For fibrosis studies, male C57BL/6J mice were deeply anesthetized using a ketamine/xylazine mixture, and the larynx was well visualized under a fiber optic light source before endotracheal intubation with a 3/400 24-gauge plastic catheter. $10^7$ CFU of lentivirus encoding genes for Empty (E), FIEL1, CON shRNA, or KIAA0317 shRNA was given i.t. for 144 h before administration of bleomycin (0.02 U~0.05 U i.t.) for up to 21 days. Animals were euthanized and assayed for BAL protein, cell count, cytokines, and lung infiltrates. Survival studies were performed on mice that were given bleomycin (0.02 U~0.05 U i.t.). Mice were carefully monitored over time; moribund, preterminal animals were immediately euthanized and recorded as deceased. For drug studies, mice were deeply anesthetized as above. Bleomycin (0.05 U i.t.) was given i.t. before BC-1480 or BC-1485 (5 mg/kg/d) was administered to the mice through their drinking water. 7-21 d later, animals were euthanized and analyzed as above.

Statistical Analysis: Statistical comparisons were performed with unpaired 2 t-test with $p<0.05$ indicative of significance. Survival curve was generated through SPSS (IBM).

Example 1

Compound Synthesis

BC1481 synthesis: 1 mmol BC-1480 (4-(2-Oxo-2,3-dihydro-1H-benzoimidazole-5-sulfonylamino) was mixed with 1.1 mmol DL-2-Amino-1-(pyrrolidin-1-yl)propan-1-one in 2 ml of DMF. 3 mmol of Et3N and 3 mmol of HBTU were then added to the mixture and stirred at RT for 18 h. Products were isolated using chromatography (CHCl3: MeOH 4:1) and dried by vacuum suction to obtain the desired product as a white powder (0.22 g, 52% yield).

BC1485 synthesis: A mixture of BC-1480 4-(2-oxo-2,3-dihydro-1H-benzo[d]imidazole-5-sulfonamido)benzoic acid (66 mg. 0.2 mmol), N-(3-Dimethylaminopropyl)-N-ethylcarbodiimide hydrochloride (38.3 mg, 0.2 mmol) and 1-Hydroxybenzotriazole hydrate (30.6 mg, 0.2 mmol) in DMF (3 mL) was stirred at room temperature for 10 min followed by addition of 2-amino-N,N-dimethylpropanamide hydrochloride (37 mg, 0.24 mmol) and triethylamine (24.3 mg. 0.24 mmol). The reaction was stirred at room temperature under nitrogen overnight. It was concentrated under vacuum. The residue was dissolved in dichloromethane (1 mL) and purified by flash chromatography (silica gel, toluene/2-propanol/ ammonia hydroxide=80/20/1, v/v/v) to obtain a sticky white solid. It was suspended in 2N HCl (2 mL), sonicated for 10 min and filtered. The wet cake was washed with water several times and dried by vacuum suction to obtain the desired product as a white powder (30 mg, 35% yield).

BC1486 synthesis: 1 mmol BC-1480 (4-(2-Oxo-2,3-dihydro-1H-benzoimidazole-5-sulfonylamino) was mixed with 1.1 mmol N1,N1-dimethylvalinamide in 2 ml of DMF. 4 mmol of DIPEA and 1.1 mmol of HATU were then added to the mixture and stirred at RT for 18 h. Products were isolated using chromatography (CHCl3:MeOH 4:1) and dried by vacuum suction to obtain the desired product as a white powder (0.19 g, 38% yield).

BC1488 synthesis: 1 mmol BC-1480 (4-(2-Oxo-2,3-dihydro-1H-benzoimidazole-5-sulfonylamino) was mixed with 1.1 mmol 2-Amino-N-benzyl-DL-propanamide in 2 ml of DMF. 4 mmol of DIPEA and 1.1 mmol of HATU were then added to the mixture and stirred at RT for 18 h. Products were isolated using chromatography (CHCl3:MeOH 6:1) and dried by vacuum suction to obtain the desired product as a yellow powder (0.35 g, 69% yield).

BC1489 synthesis: 1 mmol BC-1480 (4-(2-Oxo-2,3-dihydro-1H-benzoimidazole-5-sulfonylamino) was mixed with 1.1 mmol 2-amino-N,N-dimethyl-3-phenylpropanamide in 2 ml of DMF. 4 mmol of DIPEA and 1.1 mmol of HATU were then added to the mixture and stirred at RT for 18 h. Products were isolated using chromatography (CHCl3: MeOH 6:1) and dried by vacuum suction to obtain the desired product as a yellow powder (0.25 g, 51% yield).

DL-2-Amino-1-(pyrrolidin-1-yl)propan-1-one: 1 mmol BC-1480 (4-(2-Oxo-2,3-dihydro-1H-benzoimidazole-5-sulfonylamino) was mixed with 1.05 mmol alaninamide in 2 ml of DMF. 3 mmol of DIPEA and 1.05 mmol of HATU were then added to the mixture and stirred at RT for 18 h. Products were isolated using chromatography (CHCl3:MeOH 4:1). Yield (0.24 g, 55%). High resolution ESI-MS: 432.1340. Calculated for C19H22O5N5S+ [M+H+].

Example 2

FIEL1-PIAS4 Pathway in Pulmonary Fibrosis

Figure 9:
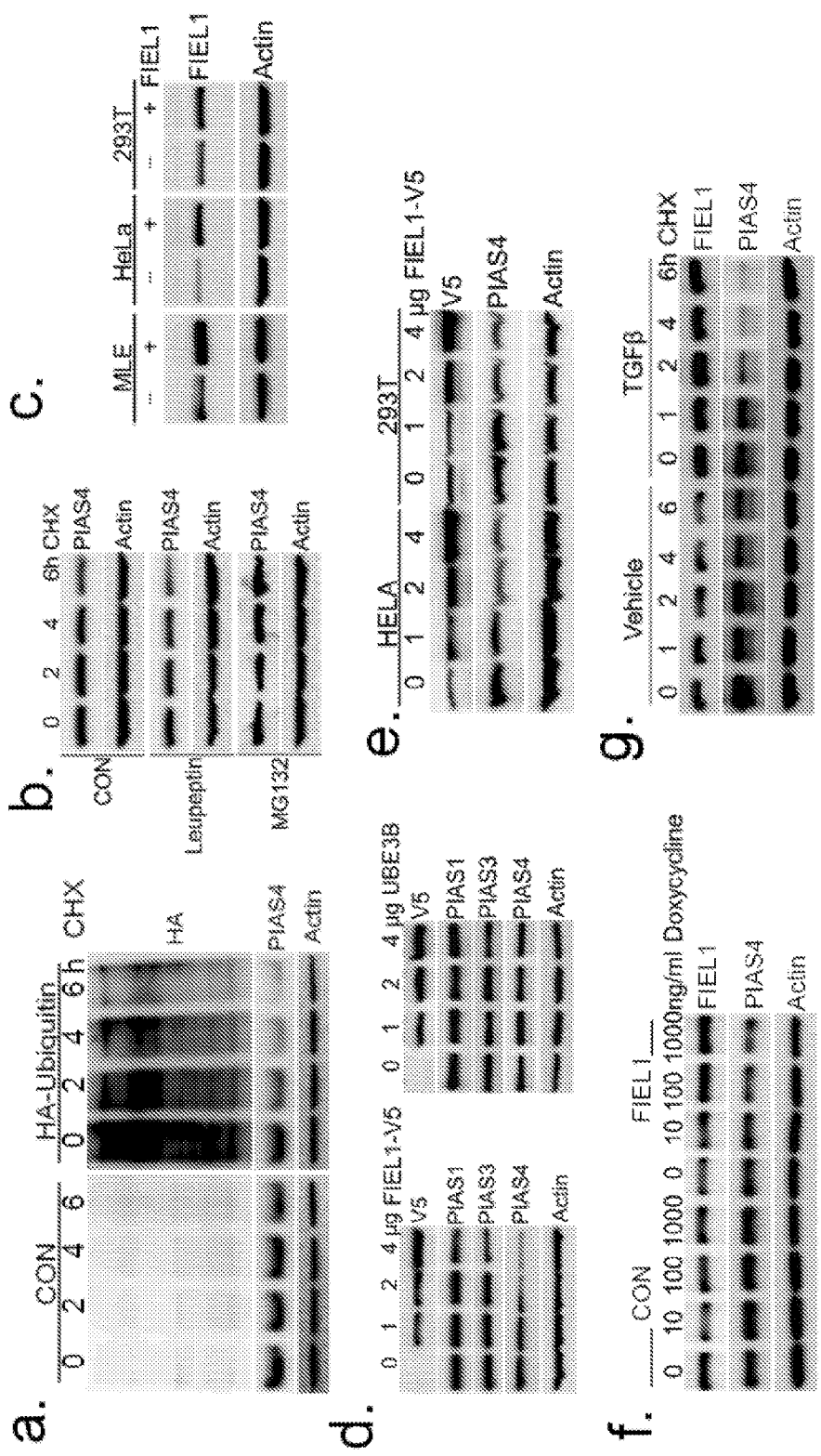
FIGS. 9A-G shows that the expression of FIEL1 reduces the half-life of PIAS4.

Ubiquitin was overexpressed, which decreases PIAS4 $t_{1/2}$ from ~6 h to 2 h. The degradation of PIAS4 occurs in a ubiquitin-dependent (FIG. 9A). Specifically, this occurs through the proteasome as addition of the proteasomal inhibitor MG132 to cells significantly increased PIAS4 protein half-life, an effect unobserved with the addition of the lysosomal inhibitor Leupeptin (FIG. 9B).

Figure 1:
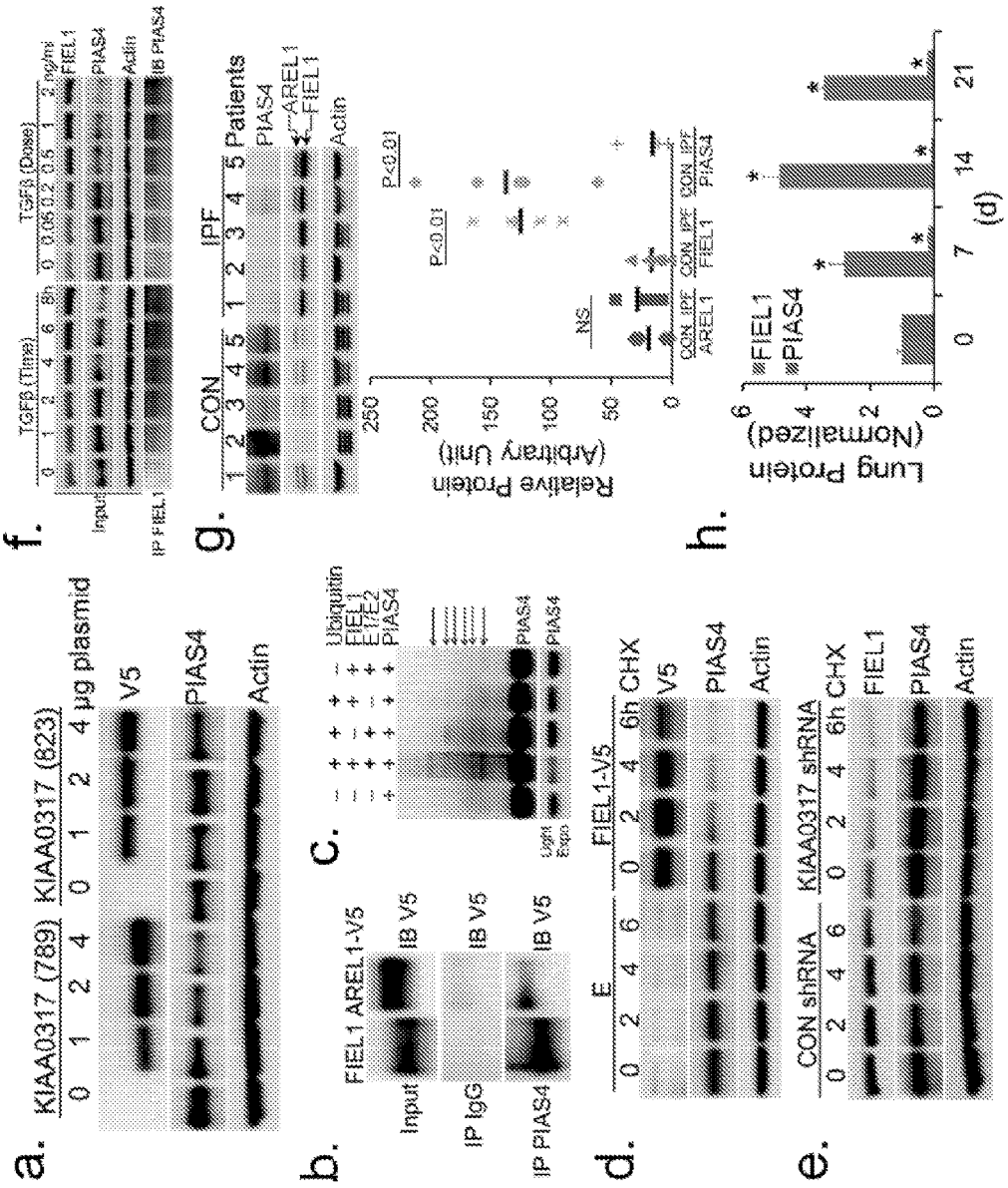
FIGS. 1A-H show in vitro and in vivo studies of FIEL1 regulating PIAS4 in pulmonary fibrosis pathway.

E3 ligases potentially involved in PIAS4 ubiquitination were screened. It was determined that the HECT domain E3 ligase KIAA0317 regulates PIAS4 protein stability (data not shown). Interestingly, KIAA0317 encodes two major isoforms, 823aa and 789aa and a previous study revealed that the longer form (823aa, termed AREL1) of KIAA0317 regulates the ubiquitination of the apoptosis proteins SMAC, HtrA2, and ARTS, as described in Kim et al., *J. Biol. Chem.*, 288(17): 12014-12021 (2013). However, it is found that the shorter isoforms (789aa, termed FIEL1, Fibrosis Inducing E3 Ligase 1) behave distinctly in cells. First, only overexpression of the shorter isoform of KL140317 (FIEL1 ) decreased PIAS4 protein levels (FIG. 1A). Compared to AREL1, FIEL1 interacted with much more PIAS4 protein in an in vitro pull down assay (FIG. 1B). Moreover, overexpression of FIEL1 in murine lung epithelial cells (MLE), HeLa and 293T co-migrated with the endogenous protein, which suggested that FIEL1 is the predominant KIAA0317 isoform in all of these cell lines (FIG. 9C). FIEL1 regulates PIAS4 ubiquitination in vitro (FIG. 1C). FIEL1 expression selectively decreased PIAS4, over other family members, in a dose-dependent manner in MLE cells (FIG. 9D). A randomly selected HECT E3 ligase, UBE3B, was also tested as a negative control (FIG. 9D). FIEL1 expression in HeLa and 293T cells also decreased PIAS4 protein levels (FIG. 9E). Conditional expression of FIEL1 in MLE cells using a doxycycline-inducible plasmid resulted in PIAS4 protein degradation in a doxycycline dose-dependent manner (FIG. 9F). Further, FIEL1 expression dramatically decreased PIAS4 protein levels, whereas FIEL1 knockdown using shRNA stabilized PIAS4 (FIGS. 1D-E) but had no effect on PIAS4 mRNA levels (data not shown). TGFβ treatment increased FIEL1 protein and decreased PIAS4 protein in both a dose and time-dependent manner in human primacy lung fibroblast MRC5 cells (FIG. 1F). TGFβ treatment also increased the association of PIAS4 and FIEL1 (FIG. 1F). Last, TGFβ treatment drastically prolonged FIEL1 protein $t_{1/2}$, and also decreased PIAS4 protein $t_{1/2}$ (FIG. 9G).

Figure 10:
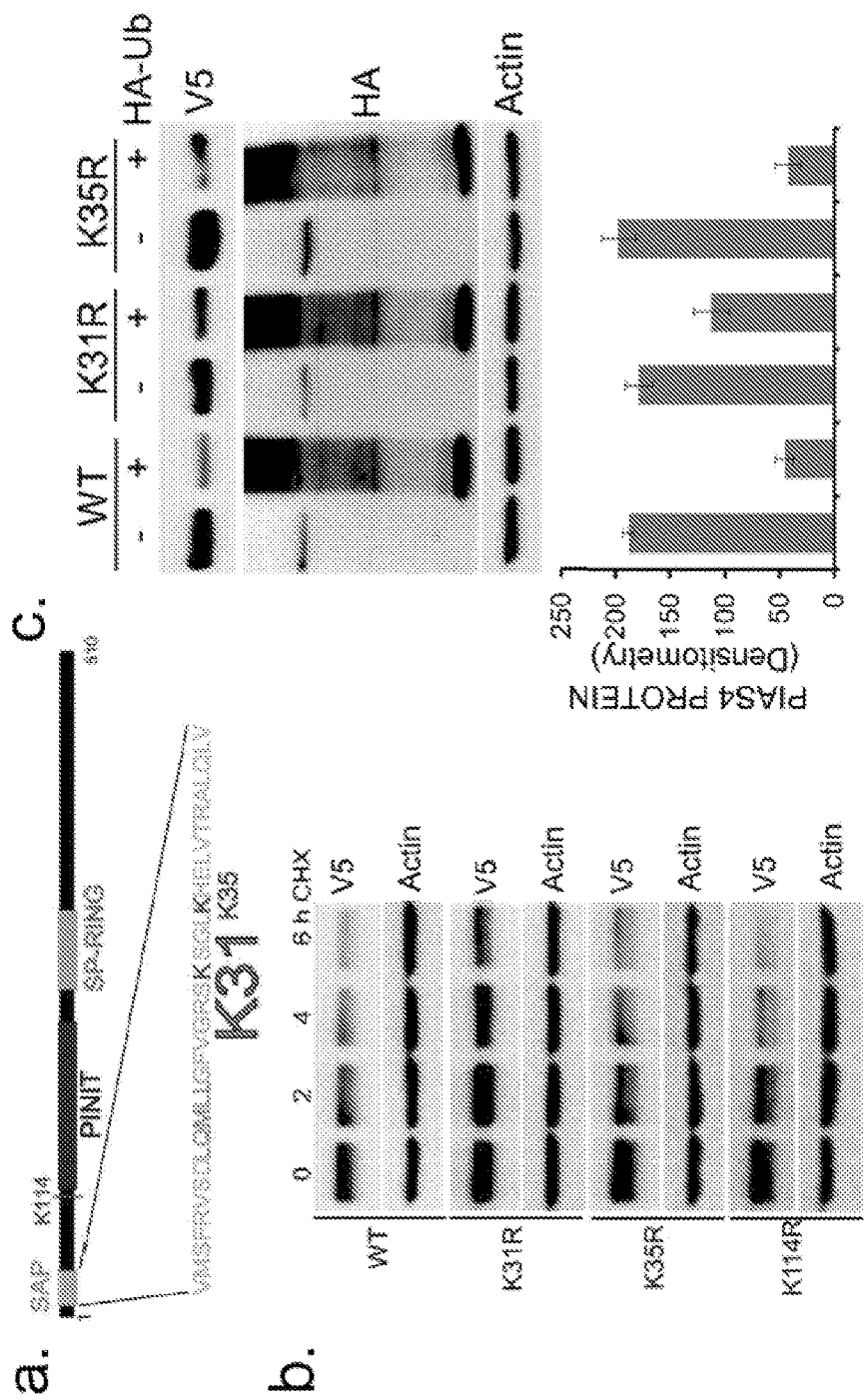
FIGS. 10A-C shows that the expression of FIEL1 does not reduce the half-life of PIAS4 with K31R mutation.

To identify the ubiquitin acceptor site within PIAS4, a candidate mapping approach was used in which PIAS4 lysine mutants were constructed and tested using various assays (FIG. 10A). The PIAS4 K31R mutant exhibited an extended $t_{1/2}$ compared to wild-type PIAS4 (FIG. 10B). Of several PIAS4 point mutants tested, only PIAS4 K31R exhibited partial resistance to ubiquitin degradation (FIG. 10C). To confirm the significance of the FIEL1-PIAS4 pathway in vivo, FIEL1 and PIAS4 protein levels in lung tissues from five control subjects and five subjects with IPF were assayed. Subjects with IPF had significantly less PIAS4 protein and more immunoreactive FIEL1 protein in their lungs versus control subjects (FIG. 1G). This pathway was also tested in bleomycin induced murine lung fibrosis, as described in Tager et al., *Nat. Med.*, 14(1):45-54 (2008); and Jiang et al., *J. Clinical Investigation*, 120(6):2049-2057 (2010). Bleomycin challenge significantly increased FIEL1 protein levels and decreased PIAS4 protein levels in mice lungs with a maximum effect at day 14 (FIG. 1H). These results suggest that the FIEL1-PIAS4 pathway is functional and important in individuals with IPF.

Example 3

FIEL1 Promotes TGFβ Signaling

Figure 2:
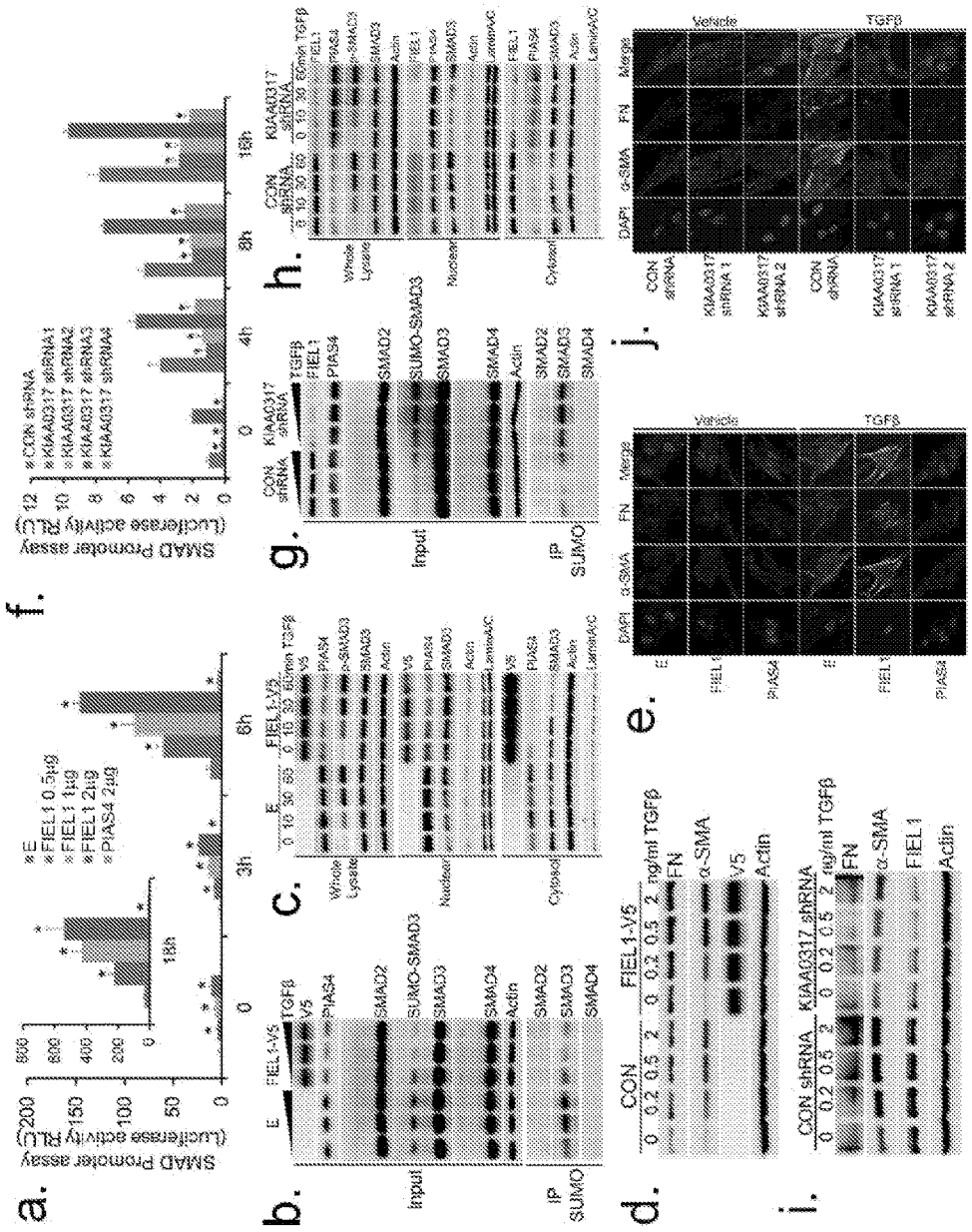
FIGS. 2A-J show SMAD reporter assays suggesting that FIELS promotes TGFβ signaling.

FIEL1 promoting TGFβ signaling was investigated by measuring SMAD transcriptional activity using a SMAD reporter assay (Qiagen). FIEL1 overexpression increased SMAD driven luciferase activity upon TGFβ stimulation in a dose dependent manner (FIG. 2A). By decreasing PIAS4 protein, expression of FIEL1 also decreased SMAD3 sumoylation (FIG. 2B) and further promoted SMAD3 nuclear import (FIG. 2C). Upon FIEL1 expression, fibrotic markers Fibronectin (FN) and alpha smooth muscle actin (α-SMA) in MRC5 cells were measured. FIEL1 expression increased the expression of FN and α-SMA (FIG. 2D). This was also confirmed by FN and α-SMA immunostaining in MRC5 cells (FIG. 2E). When FIEL1 is knockdown using several shRNAs, a significantly reduced SMAD driven luciferase activity was observed (FIG. 2F). FIEL1 knockdown increased PIAS4 protein, increased SMAD3 sumoylation (FIG. 2G), and further decreased SMAD3 nuclear import (FIG. 2H). FIEL1 knockdown also reduced FN and α-SMA expression in MRC5 cells upon TGFβ treatment (FIGS. 2I, J).

Example 4

PIAS4 Phosphorylation by PKCξ is Required for FIEL1 Binding

Figure 3:
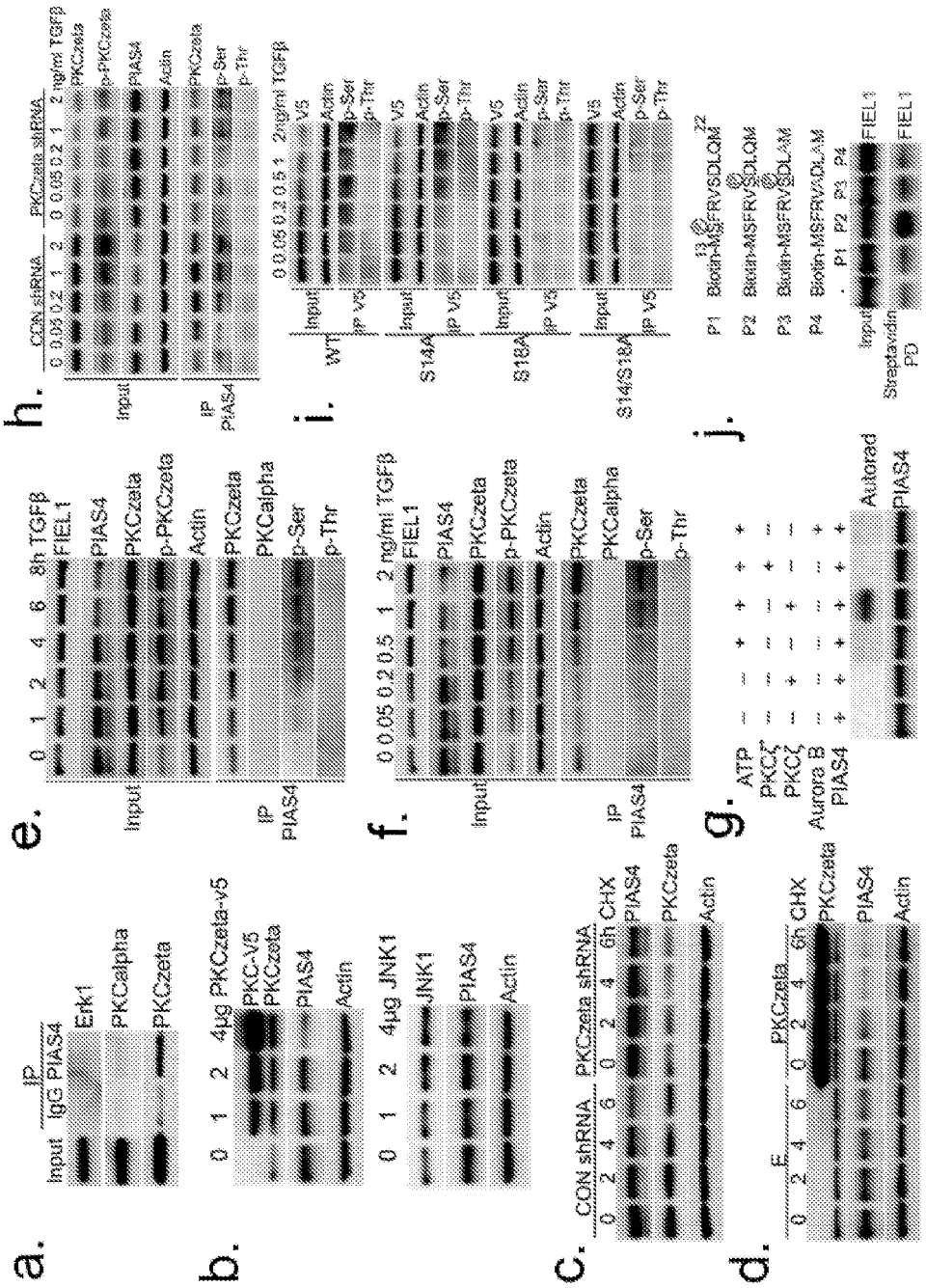
FIGS. 3A-J shows that PIAS4 phosphorylation by PKCξ is required for FIEL1 binding.

The FIEL1 binding site within PIAS4 was investigated. Mapping studies were by constructing several deletional mutants of PIAS4 and cloning them into a pcDNA3.1D/V5-HIS vector (FIG. S3A). It was determined that FIEL1 binds within the N-terminal 25 amino acids of PIAS4 (FIG. S3B, lower blot). An alanine scan study within this region suggested that both S18 and Q21 are important for FIEL1 interaction, as both S18A and Q21A mutants drastically lost binding with FIEL1 (FIG. S3C). A kinase screen was performed and it was determined that PKCξ interacts with PIAS4 via Co-IP (FIG. 3A). Erk1 and PKCα were also included as specificity controls. PKCξ expression also decreased PIAS4 protein level in a dose-dependent manner, whereas JNK1 expression was not able to achieve such an effect (FIG. 3B). Moreover, PKCξ knockdown using shRNA drastically stabilized PIAS4 protein in a $t_{1/2}$ study (FIG. 3C), whereas PKCξ expression decreased PIAS4 $t_{1/2}$ to ~2 h (FIG. 3D).

To confirm that PIAS4 is phosphorylated in vitro, cells were lysed and subjected to PIAS4 IP, and using phosphoserine antibodies, a band was detected which migrated to the predicted size of PIAS4 (FIGS. 3E-F, ~60 kDa). TGFβ stimulation also drastically increased PIAS4 serine phosphorylation and PKCξ binding, but not PKCα binding (FIGS. 3E-F). It was observed that PKCξ directly phosphorylated PIAS4 in an in vitro kinase assay (FIG. 3G). PKCξ knockdown also protected PIAS4 from phosphorylation and degradation during TGFβ treatment (FIG. 3H). Compared to WT PIAS4, S18A and S14/S18A double mutant exhibited a dramatic decrease in phosphorylation and offered significant resistance to degradation during TGFβ treatment (FIG. 3I). PIAS4 S18A, Q21A, and S18/Q21A double mutants also exhibited much longer half-lives (FIG. S3D) and resisted degradation from FIEL1 co-expression (FIG. S3E). Last, a peptide binding experiment was performed in which four biotin-labeled synthetic peptides were bound to streptavidin-agarose beads and served as bait for FIEL1 binding (FIG. 3J). The peptide with S18 phosphorylation (P2) showed the strongest binding to FIEL1; the peptide with Q21 mutation (P3) offered drastically decreased FIEL1 interaction (FIG. 3J). These experiments suggested that PKCξ is an authentic regulator of PIAS4 protein stability; Q21 and phosphorylated S18 of PIAS4 are both required for FIEL1 interaction.

Example 5

GSK3β Phosphorylation of FIEL1 is Required for PIAS4 Targeting

Figure 11:
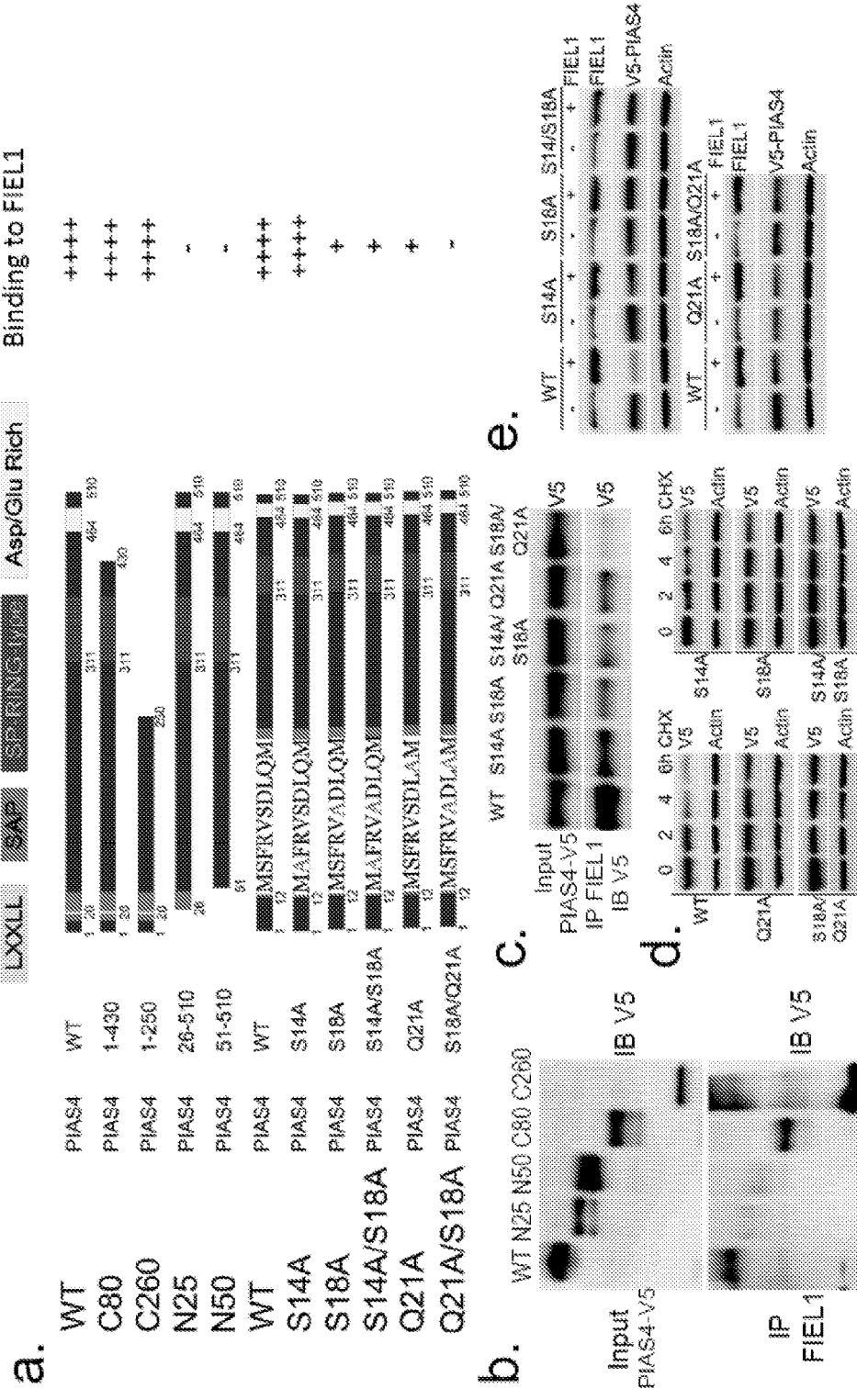
FIGS. 11A-E shows an alanine scan study of PIAS4, which suggests that both S18 and Q21 residues are important for FIEL1 interaction.

The PIAS4 binding site within FIEL1 was investigated. A similar mapping study as above was performed by constructing several deletional mutants of FIEL1 and cloning them into a pcDNA3.1D/V5-HIS vector (FIG. 11A). A mapping study was done similarly to FIG. 11 using a PIAS4 antibody to construct PIAS4 beads as the bait. It was first determined that PIAS4 binds within the last 189 residues of the C-terminal of FIEL1 (FIGS. 12B-C). Additional mapping suggested that PIAS4 interacts with the last 10 amino acids of FIEL1 (FIGS. 12D-E). An alanine scan study within this region suggested that both P779 and T783 are important for PIAS4 interaction, as both P779A and T783A mutants drastically lost binding with PIAS4 (FIG. 12F). Compared with WT FIEL1, neither P779A nor T783A mutant expression decreased PIAS4 protein levels (FIG. 12G). It was also determined that C770 is a potential active site of FIEL1 as the C770S mutant also failed to decrease PIAS4 protein level (FIG. 12G). SNP database analysis indicated a naturally occurring polymorphism (rs371610162) within FIEL1 (P779L). This mutation was further tested in a binding assay and showed that T783A, P779L, and P779L/T783A double mutant all lost interaction with PIAS4 (FIG. 12H).

Figure 4:
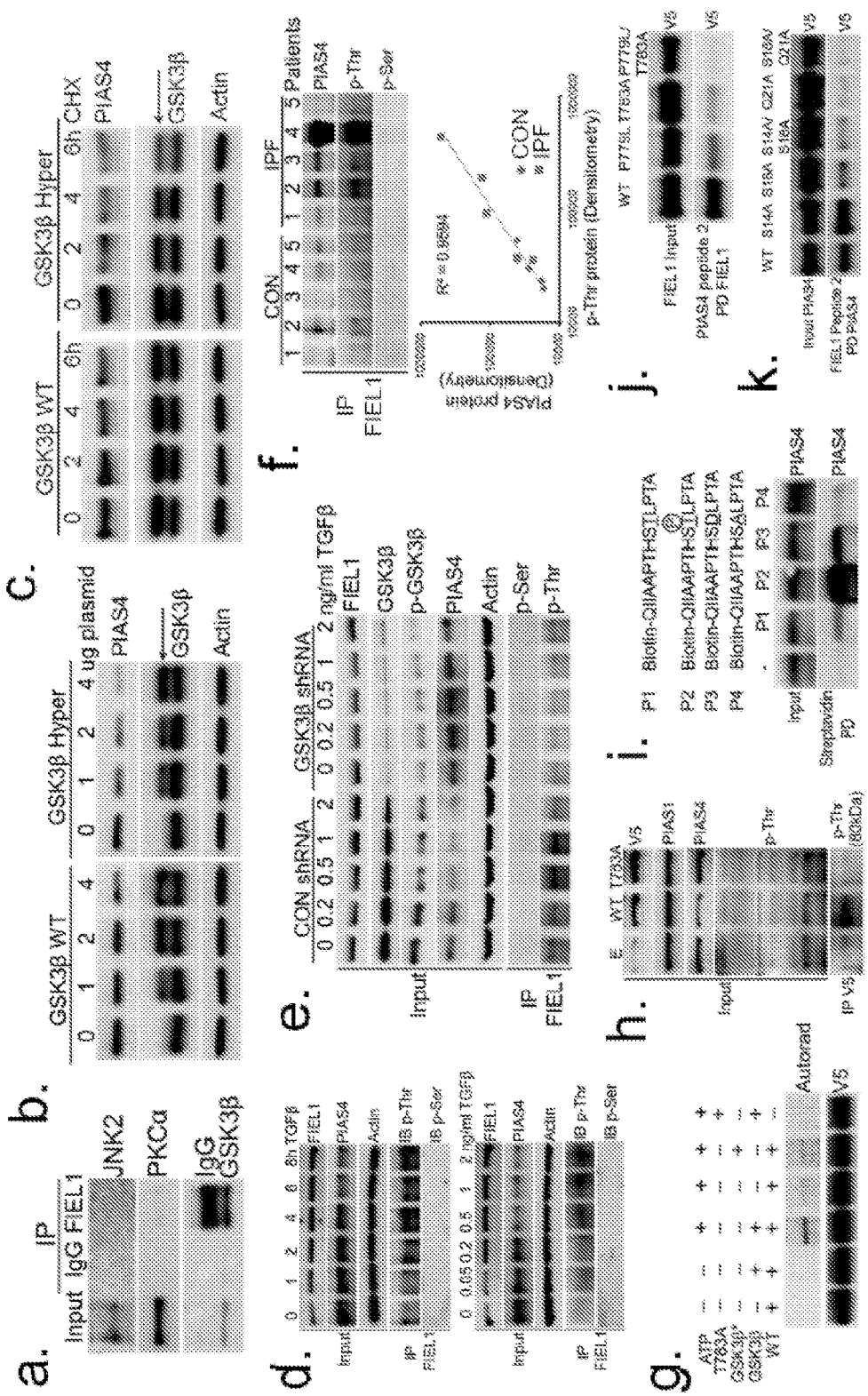
FIGS. 4A-K shows that GSK3β phosphorylation of FIEL1 is required for PIAS4 targeting, and FIEL1 residues P779 and phosphorylated T783 are both required for PIAS4 interaction.

A kinase screen was performed and it was determined that GSK3β interacts with FIEL1 via Co-IP (FIG. 4A). JNK2 and PKCα were also included as specificity controls. WT GSK3β overexpression decreased PIAS4 protein levels in a dose dependent manner, and PIAS4 protein levels decreased more dramatically when cells was transfected with a constitutively activated GSK3β hyper mutant plasmid (FIG. 4B). Moreover, a CHX $t_{1/2}$ study suggested that WT GSK3β ectopic expression decreased PIAS4 $t_{1/2}$ to ~4 h, whereas the more potent GSK3β hyper mutant further decreased PIAS4 $t_{1/2}$ to 2 h (FIG. 4C). TGFβ stimulation drastically increased FIEL1 threonine phosphorylation (FIG. 4D), and GSK3β knockdown drastically stabilized PIAS4 in a $t_{1/2}$ study (FIG. S5A). Moreover, GSK3β knockdown also protected FIEL1 from threonine phosphorylation and PIAS4 degradation with TGFβ treatment (FIG. 4E).

Figure 13:
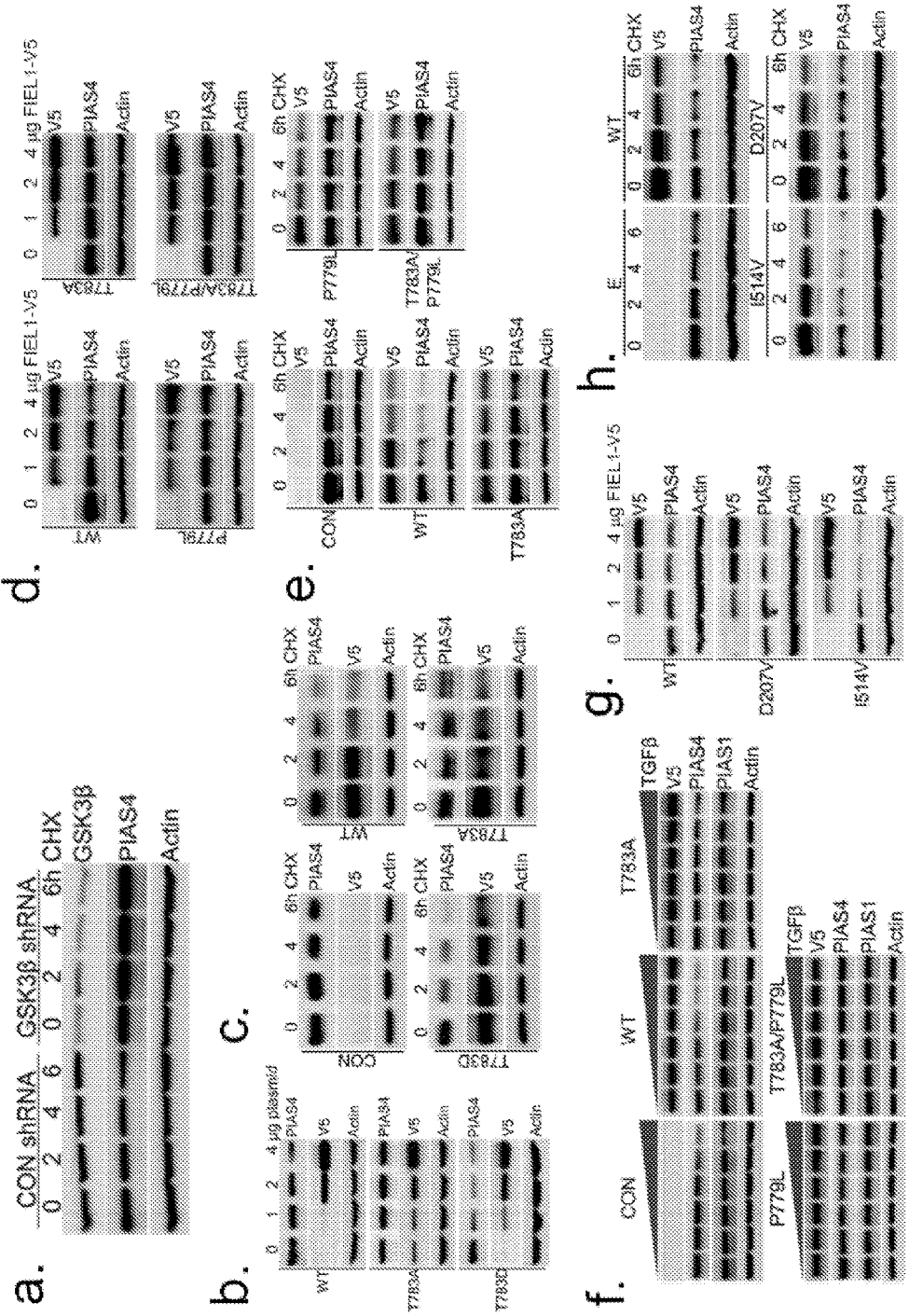
FIGS. 13A-H shows studies of FIEL1 mutations, which suggests that FIEL1 residues P779 and GSK3β phosphorylated T783 are both required for PIAS4 interaction.

Using the lung lysates from FIG. 1F, a Co-IP experiment was performed where FIEL1 protein was immunoprecipitated and immunobloted for PIAS4 and p-Thr. a positive association between PIAS4 and p-Thr signal was observed, which suggested that FIEL1 threonine phosphorylation is essential for PIAS4 binding (FIG. 4F). The role of FIEL1 T783 in regulating PIAS4 protein stability was further studied. FIEL1 T783A mutant overexpression completely failed to decrease PIAS4 protein levels. However, phosphorylation mimic T783D mutant FIEL1 expression decreased PIAS4 protein levels more dramatically compared to WT FIEL1 expression (FIG. 13B). Moreover, a $t_{1/2}$ study suggested that WT FIEL1 expression decreased PIAS4 $t_{1/2}$ to ~4 h, whereas the more potent phosphorylation mimic T783D further decreased PIAS4 $t_{1/2}$ to ~2 h (FIG. 13C). The FIEL1 T783A mutant was resistant to GSK3β phosphorylation in an in vitro kinase assay (FIG. 4G). The FIEL1 T783A mutant also exhibited drastically decreased phosphorylation in cells (FIG. 4H). A peptide binding experiment was also performed where four biotin-labeled synthetic peptides were bound to streptavidin-agarose beads and served as bait for PIAS4 binding (FIG. 4I). Peptide with phosphorylation at T783 (P2) showed the strongest binding to PIAS4; peptide with no phosphorylation (P1) or T783A mutant (P4) offered drastically decreased PIAS4 interaction. FIEL1 T783A and P779L expression both failed to decrease PIAS4 protein levels (FIG. 13D) or half-lives (FIG. S5E). FIEL1 T783A/P779L double mutant expression showed a dominant negative phenotype by increasing PIAS4 protein levels (FIG. 13D). PIAS4 peptide 2 was used with S18 phosphorylation as bait in an in vitro binding assay (FIG. 4J). Both P779L and T783A mutants drastically lost binding with PIAS4, which is similar to FIG. S4H. Similarly, FIEL1 Peptide 2 with phosphorylation at T783 (P2) was used to reconfirm the importance of S18 phosphorylation and Q21 within PIAS4 for FIEL1 interaction (FIG. 4K), which is similar to FIG. S3C. Last, FIEL1 T783A/P779L dominant negative double mutant overexpression protected PIAS4 from TGFβ treatment (FIG. 13F). These experiments suggested that the GSK3β phosphorylation of FIEL1 is required for PIAS4 targeting, and FIEL1 residues P779 and phosphorylated T783 are both required for PIAS4 interaction.

Example 6

Gene Transfer of FIEL1 Exacerbates Bleomycin Induced Lung Injury In Vivo

This example considers whether expression of FIEL1 in vivo alters host inflammatory responses and induce fibrotic lung injury. To extend the above observations in vivo, mice were infected with an empty lentivirus or lentivirus encoding FIEL1 for 144 h ($10^7$ cfu/mouse, intratracheally [i.t.]). Mice were then challenged with bleomycin (0.02 U i.t) for an additional 1-21 days. Mice were euthanized to analyze parameters of fibrotic lung injury.

Figure 5:
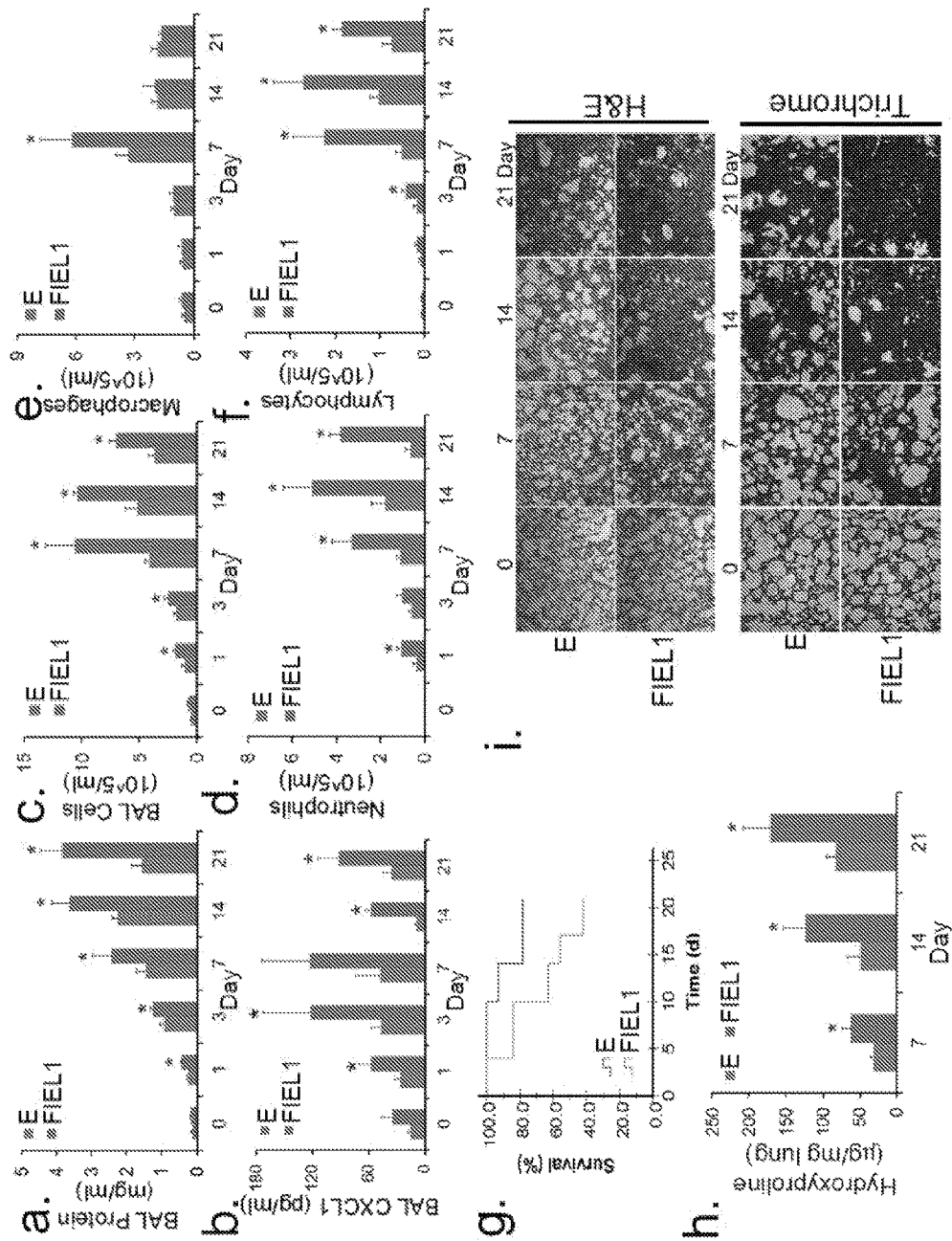
FIGS. 5A-I shows that in vivo expression of FIEL1 exacerbates bleomycin induced lung injury. C57BL/6J mice were administered i.t. with Lenti-Empty or Lenti-FIEL1 ($10^7$ PFU/mouse) for 144 h; mice were then administered i.t. with bleomycin (0.02 U) for 1-21 days. Mice were euthanized, and lungs were lavaged with saline, harvested, and then homogenized. Lavage protein and CXCL1 concentrations were measured in FIGS. 5A-B. Lavage total cell counts were measured in (FIG. 5C). Lavage cells were then processed for Wright-Giemsa stain; Lavage macrophages, neutrophils, and lymphocytes were counted and graphed (FIGS. 5D-F).

Bleomycin has been wildly used to study IPF in murine models. As shown in FIG. 5A, the increased BAL total protein concentration that occurs after bleomycin injury in control mice was significantly increased in mice overexpressing FIEL1. Chemokine CXCL1 levels in BALs were also significantly increased in mice overexpressing FIEL1 (FIG. 5B). A similar increase in IL-6 levels in BALs from mice overexpressing FIEL1 was also observed (data not shown). The role of FIEL1 in the lung's inflammatory response to bleomycin was investigated (FIGS. 5C-F). A marked increase in total inflammatory cells in the BAL fluid from mice overexpressing FIEL1 was observed (FIG. 5C). Specifically, the differential cell counts of the BALs revealed that the total increase in inflammatory cells was mostly due to neutrophils and lymphocytes, with the exception of macrophages on day 7 (FIGS. 5D-F). FIEL1 expression in mice also significantly reduced survival (FIG. 5G). A marked increase in lung fibrosis in mice overexpressing FIEL1 as demonstrated by significantly increased hydroxyproline content was observed (FIG. 5H). Bleomycin challenge also showed changes consistent with peribronchiolar and parenchymal fibrosis in a time-dependent manner (FIGS. 5I, H&E). The extent of these changes present in FIEL1 expression mice was substantially increased as compared to the empty control (FIGS. 5I, H&E). Elevated lung collagen visualized by Mason Trichrome staining also suggested that FIEL1 expression exacerbates bleomycin-induced lung injury (FIG. 5I, Trichrome).

Example 7

FIEL1 Knockdown Ameliorates Bleomycin-Induced Lung Injury In Vivo

To further confirm the role of FIEL1 in lung fibrosis and inflammation, in vivo knockdown studies were pursued. Mice were first infected with lentivirus encoding CON shRNA or KIAA0317 shRNA for 144 h ($10^7$CFU/mouse, i.t) and then challenged with bleomycin (0.05 U i.t.) for an additional 1-21 days.

Figure 6:
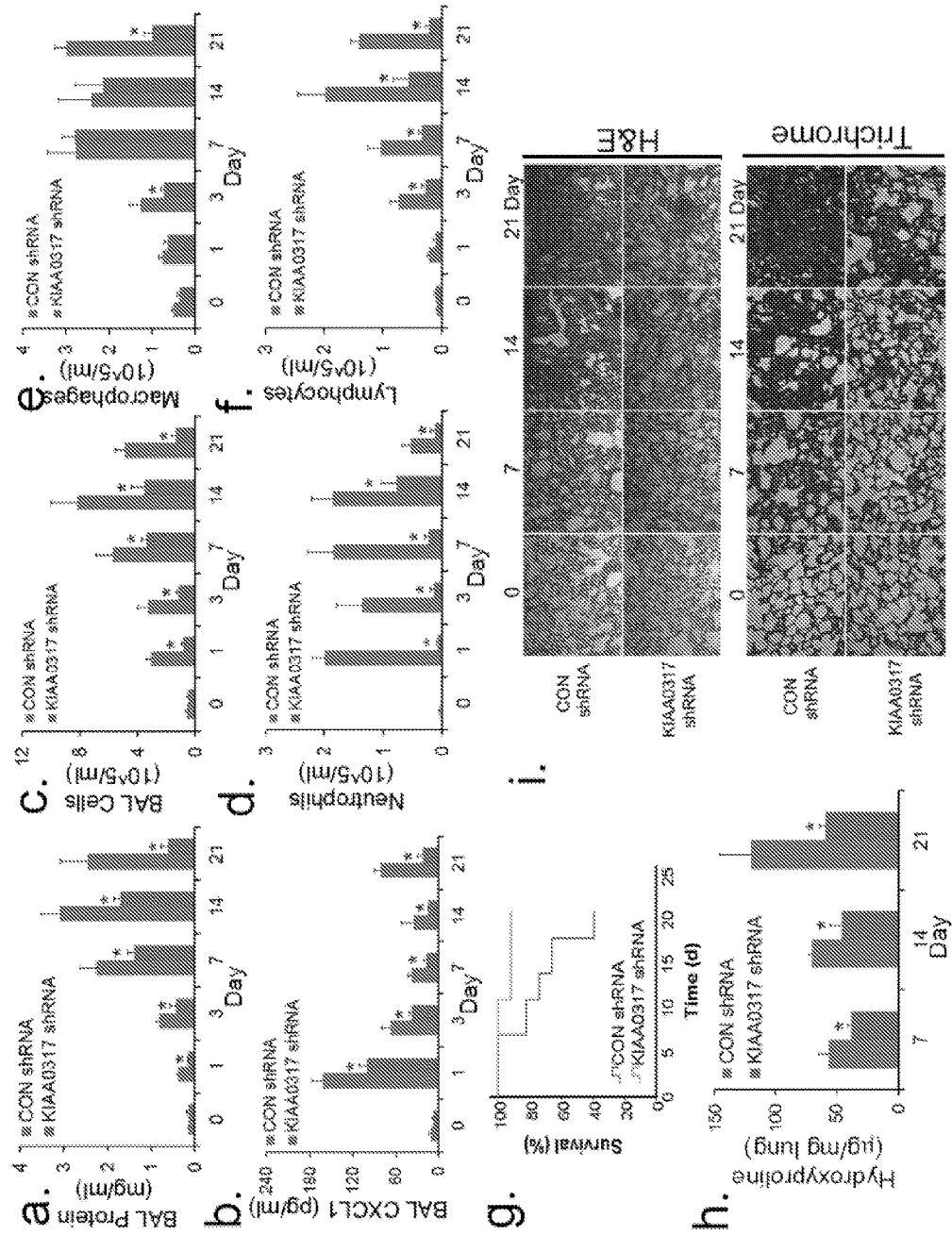
FIGS. 6A-I shows that a decrease in expression of FIEL ameliorates bleomycin-induced lung injury in vivo. C57BL/6J mice were administered i.t. with Lenti-CON shRNA or Lenti-KIAA0317 shRNA ($10^7$ PFU/mouse) for 144 h; mice were then administered i.t. with bleomycin (0.05 U) for 1-21 days. Mice were euthanized, and lungs were lavaged with saline, harvested, and then homogenized. Lavage protein and CXCL1 concentrations were measured in FIGS. 6A-B. Lavage total cell counts were measured in (C). Lavage cells were then processed for Wright-Giemsa stain; Lavage macrophages, neutrophils, and lymphocytes were counted and graphed (FIGS. 6D-F).

FIEL1 knockdown significantly decreased BAL protein concentrations and Chemokine CXCL1 levels (FIGS. 6A, B). FIEL1 knockdown also significantly decreased BAL total cell counts (FIG. 6C). Specifically, the differential cell counts of BALs revealed that the total decrease in inflammatory cells was mostly due to neutrophils and lymphocytes, with the exception of macrophages on day 3 and 21 (FIGS. 6D-F). FIEL1 knockdown in mice also significantly improved survival (FIG. 6G). A marked decrease in lung fibrosis in FIEL1 knockdown mice as demonstrated by a significant decrease in hydroxyproline content was observed (FIG. 6H). Peribronchiolar and parenchymal fibrosis were also substantially decreased in FIEL1 knockdown mice (FIGS. 6I, H&E). Decreased lung collagen visualized by Mason Trichrome staining also suggested that FIEL1 knockdown ameliorates bleomycin-induced lung injury (FIG. 6I, Trichrome).

Example 8

FIEL1 Domain Analysis and Inhibitor Design

Figure 7:
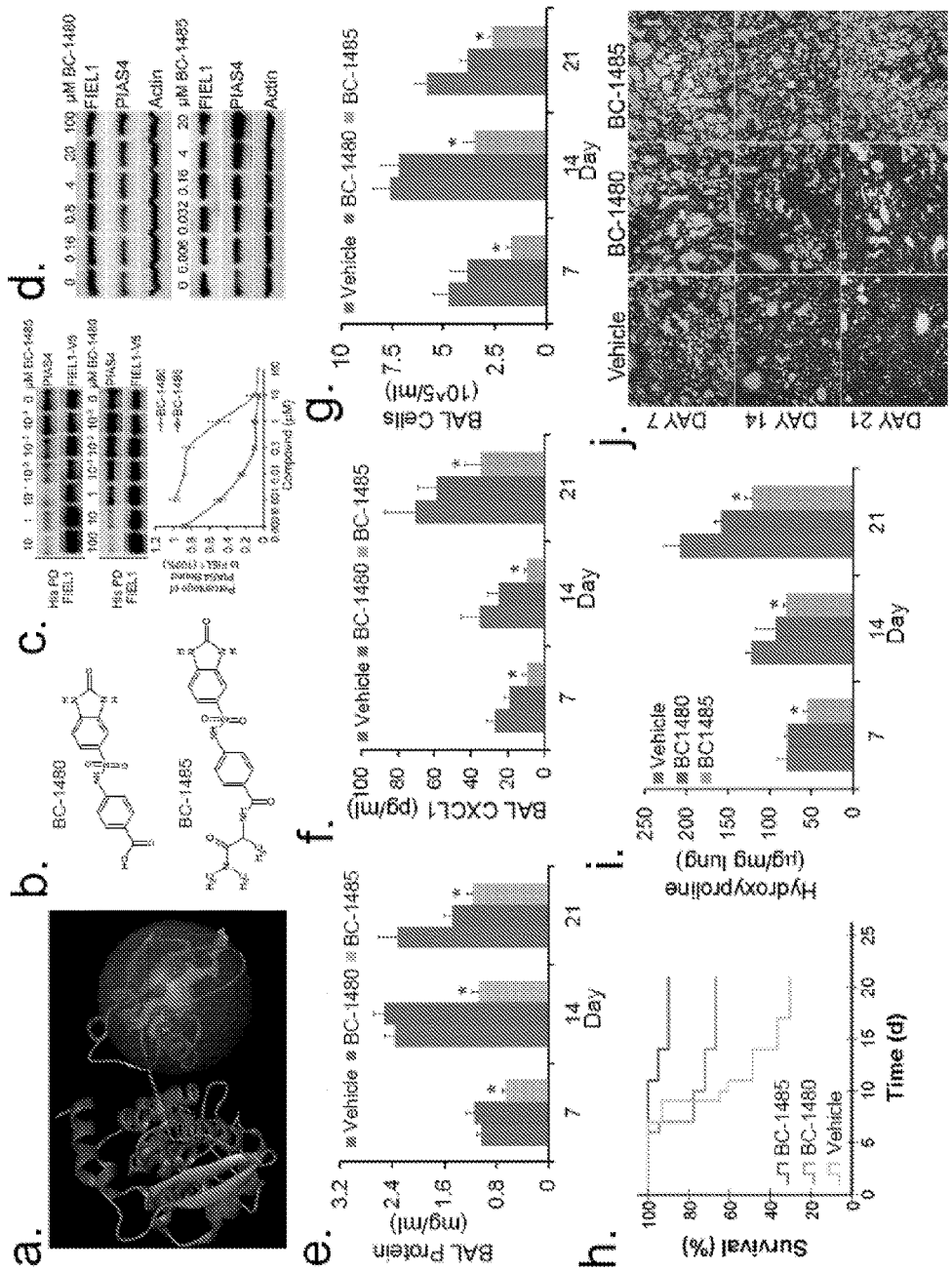
Figure 8:
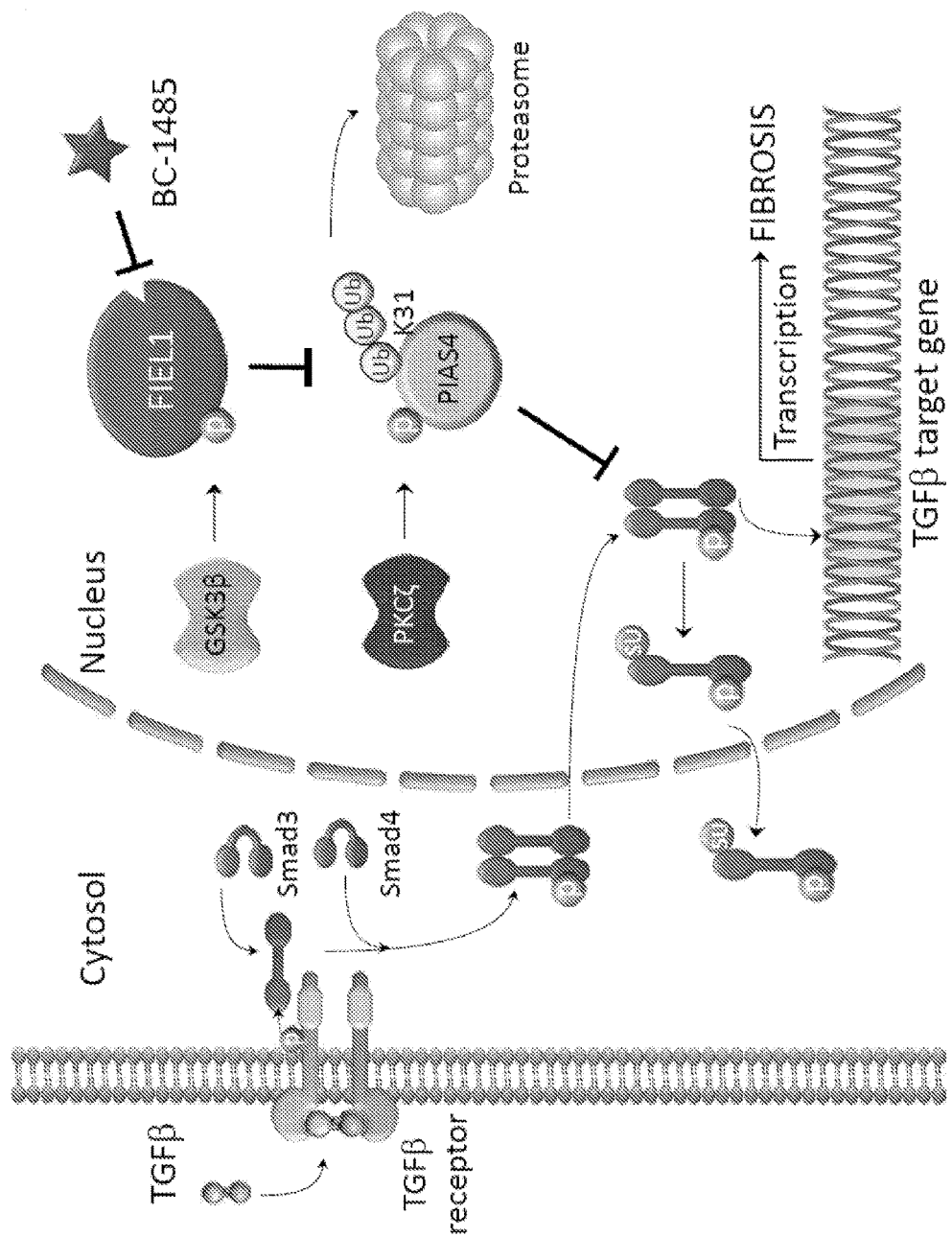
FIG. 8 shows molecular regulation of TGFβ signaling mediated by FIEL1.
Figure 12:
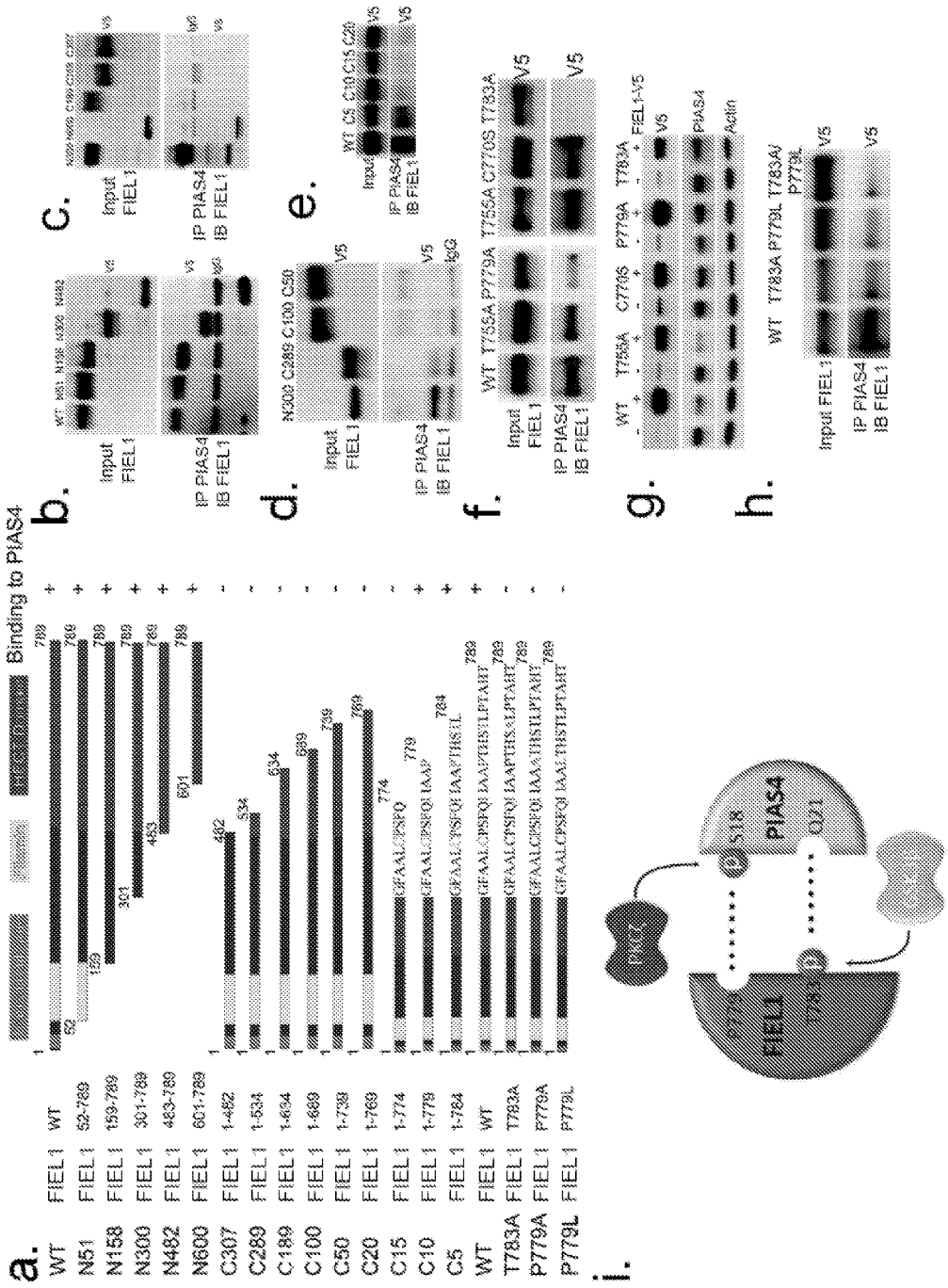
FIGS. 12A-H shows studies of PIAS4 mutations, which suggests that both Q21 residue and PKCξ phospharylated S18 residue are required for FIEL1 binding.
FIG. 12I. The cartoon illustrates the "double locking" molecular interplay between PIAS4 and FIEL1. Specifically, both the P779 and GSK3β phosphorylated T783 residues within FIEL1 are required for PIAS4 binding; both the Q21 and PKCξ phosphorylated S18 residues within PIAS4 are required for FIEL1 binding.

This example tests that small molecule inhibition of the HECT domain would disrupt FIEL1 targeting its substrate, PIAS4, because FIEL1 harbors a conserved HECT domain within its C-terminus which carries out the E3 ligase activity of transferring ubiquitin to the substrate. A homology model using the NEDD4 HECT domain was first constructed (2XBF.pdb) (FIG. 7A). NEDD4 HECT domain was described in Umadevi N et al. *Acta crystallographica Section F, Structural biology and crystallization communications*, 61(Pt 12): 1084-1086 (2005), and Kamadurai HB et al. *Molecular cell*. 36(6): 1095-1102 (2009). A major cavity within the C-terminal of the FIEL1 HECT domain was observed, which is also required for PIAS4 binding (FIG. 12). Using molecular docking analysis and score-ranking operations on the predicted FIEL1-HECT domain 3-D structure model, potential ligands that might fit the HECT domain cavity was assessed (FIG. 7A).

Figure 15:
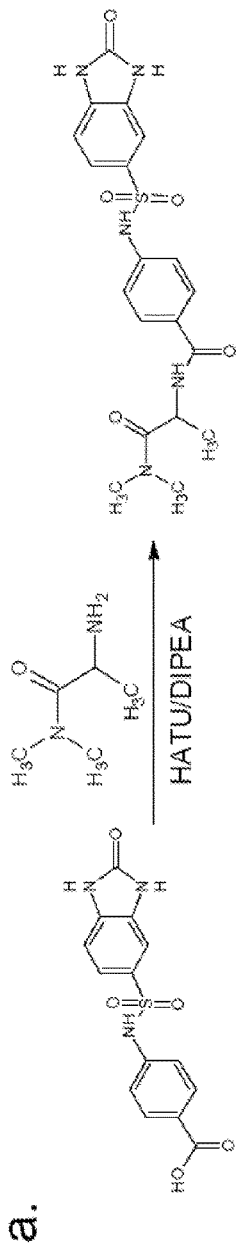
FIGS. 15A-G shows the synthesis of FIEL1 inhibitor BC1485, and its inhibition of TGFβ pathway.
Figure 15:
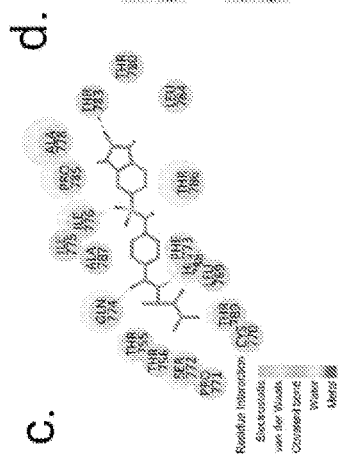
Figure 15:
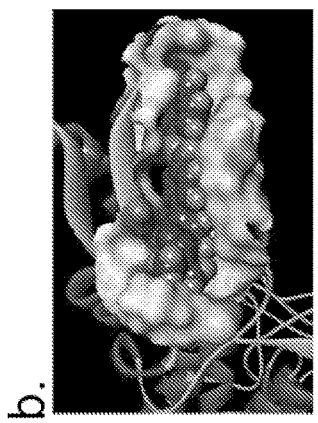
Figure 15:
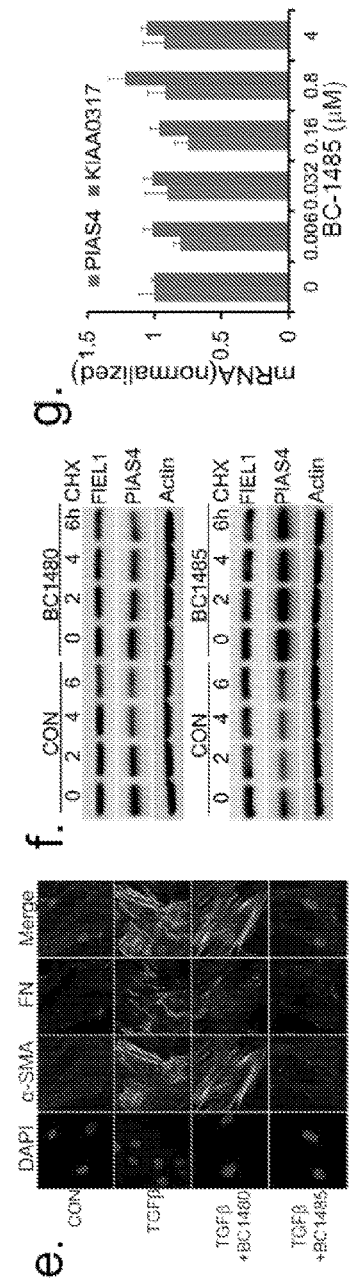

These docking experiments were conducted using the LibDock program from Discovery Studio 3.5, and a library containing 500 k small molecule compounds was first used to screen potential ligands for the FIEL1-HECT domain. 19 compounds were selective for initial round of testing. 9/19 compounds showed good activity (IC50<1 uM) blocking FIEL1 in MLE cells indicated by increase substrate PIAS4 protein (FIG. 14). BC-1480 (4-(2-Oxo-2,3-dihydro-1H-benzoimidazole-5-sulfonylamino)-benzoic acid) was further selected as a backbone to develop small-molecule inhibitors (FIG. 7B). BC-1485 was synthesized by reacting alaninamide with BC-1480 (FIG. 15A). As shown in FIGS. S7B-C, BC-1485 fits in the HECT domain cavity fairly well having several electrostatic interactions with GLN774, HIS 788, ILE 776 and THR783 (FIGS. 15B-C). Compared to BC-1480, BC-1485 exhibited >100 fold activity in disrupting the FIEL1/PIAS4 interaction (FIG. 7C) and increasing PIAS4 protein levels (FIG. 7D). Indeed, BC-1485 decreased the expression of α-SMA in MRC5 cells with $IC_{50} \approx 32$ nM, whereas BC-1480 decreased the expression of α-SMA with $IC_{50} \approx 4$ μM (FIG. 15D). This was also confirmed by FN and α-SMA immunostaining in MRC5 cells (FIG. 15E). BC-1485 also stabilized PIAS4 by extending its half-life (FIG. 15F). Last, BC-1485 did not significantly alter KIAA0317 or PIAS4 mRNA levels (FIG. 15G).

Figure 16:
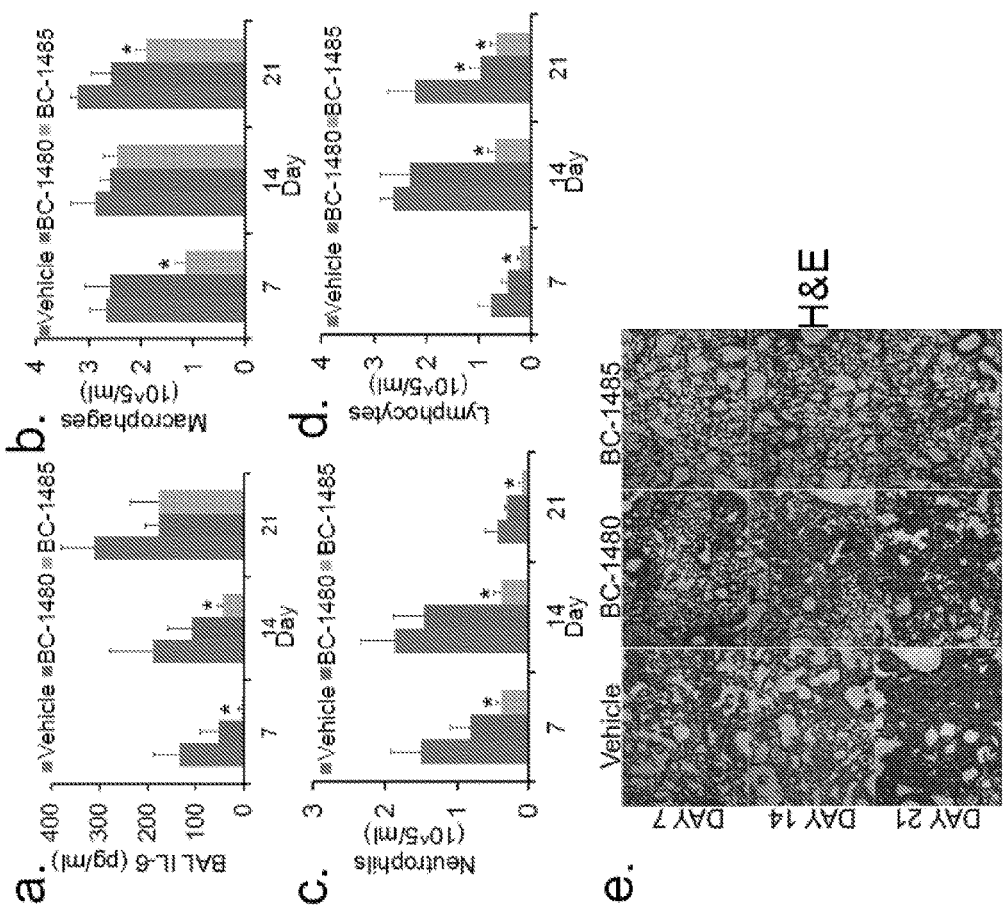
FIGS. 16A-E shows BC1480 and BC 1485 inhibition of pulmonary fibrosis in a mouse model. C57BL/6J mice were administered i.t. with bleomycin (0.05 U) for 7-21 days. Compounds BC-1480 and BC-1485 were given to mice through drinking water with an estimated dose of 5 mg/kg/d. Mice were then euthanized, and lungs were lavaged with saline, harvested, and then homogenized. Lavage IL-6 was measured in (FIG. 16A). Lavage cells were also processed for Wright-Giemsa stain; Lavage macrophages, neutrophils and lymphocytes were counted and graphed (FIGS. 16B-D). H&E staining was performed on lung samples from A. Original magnification, ×10. *p<0.05 compared to Vehicle (t test). Data are an average of two experiments (A-E, 4-8 mice/group).
Figure 17:
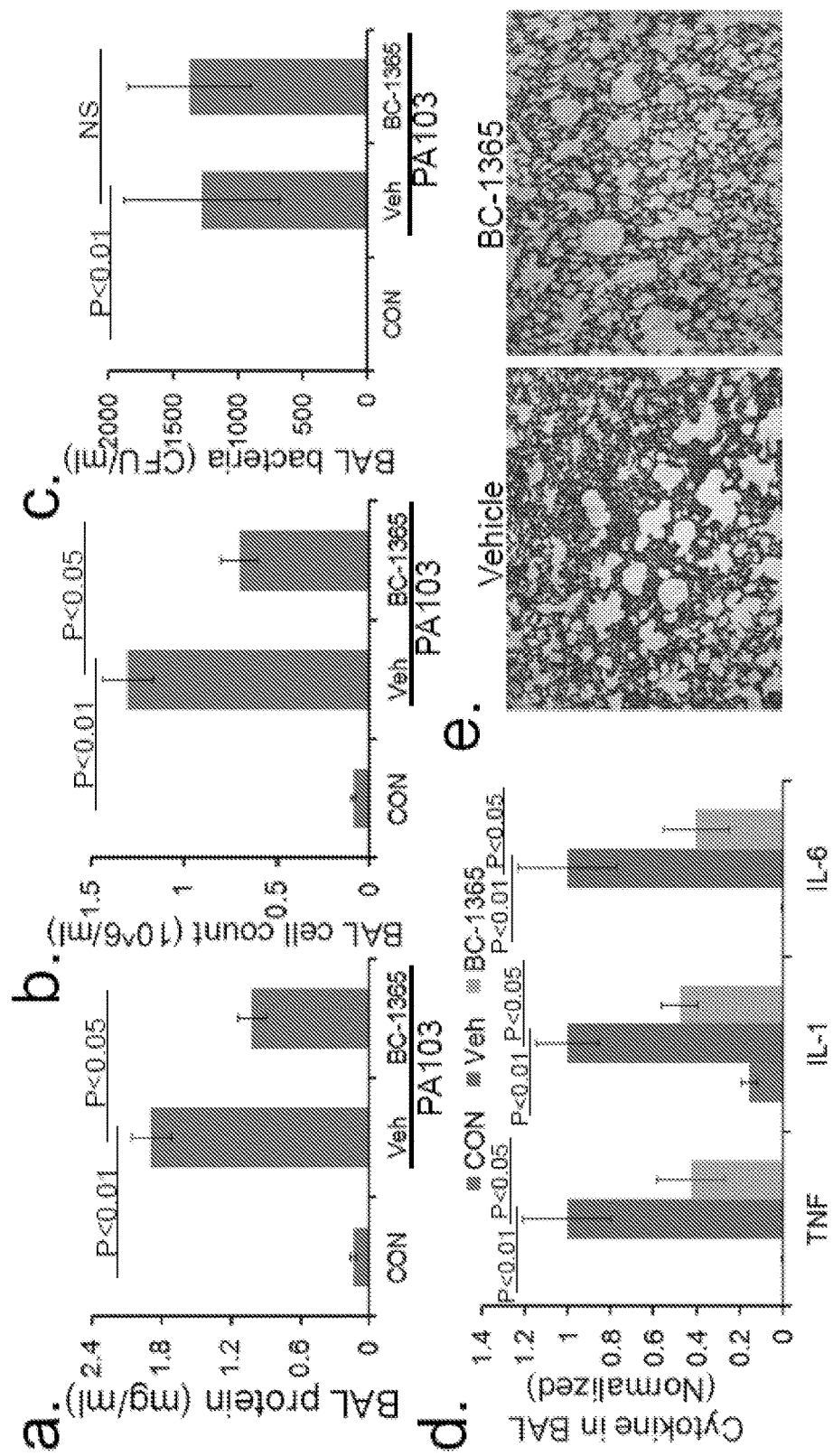
FIGS. 17A-E shows anti-inflammatory activity of a FIEL1 small molecule inhibitor in Pseudomonas pneumonia model. C57BL/6J mice were administered i.t. with PA103 (104 PFU/mouse). BC-1365 was given through IP injection (10 mg/kg) at the same time. 18 h later, mice were sacrificed, and lungs were lavaged with saline, harvested, and then homogenized. Lavage protein, cell count, bacterial count, and cytokine secretion were measured in (FIGS. 17A-D).
Figure 18:
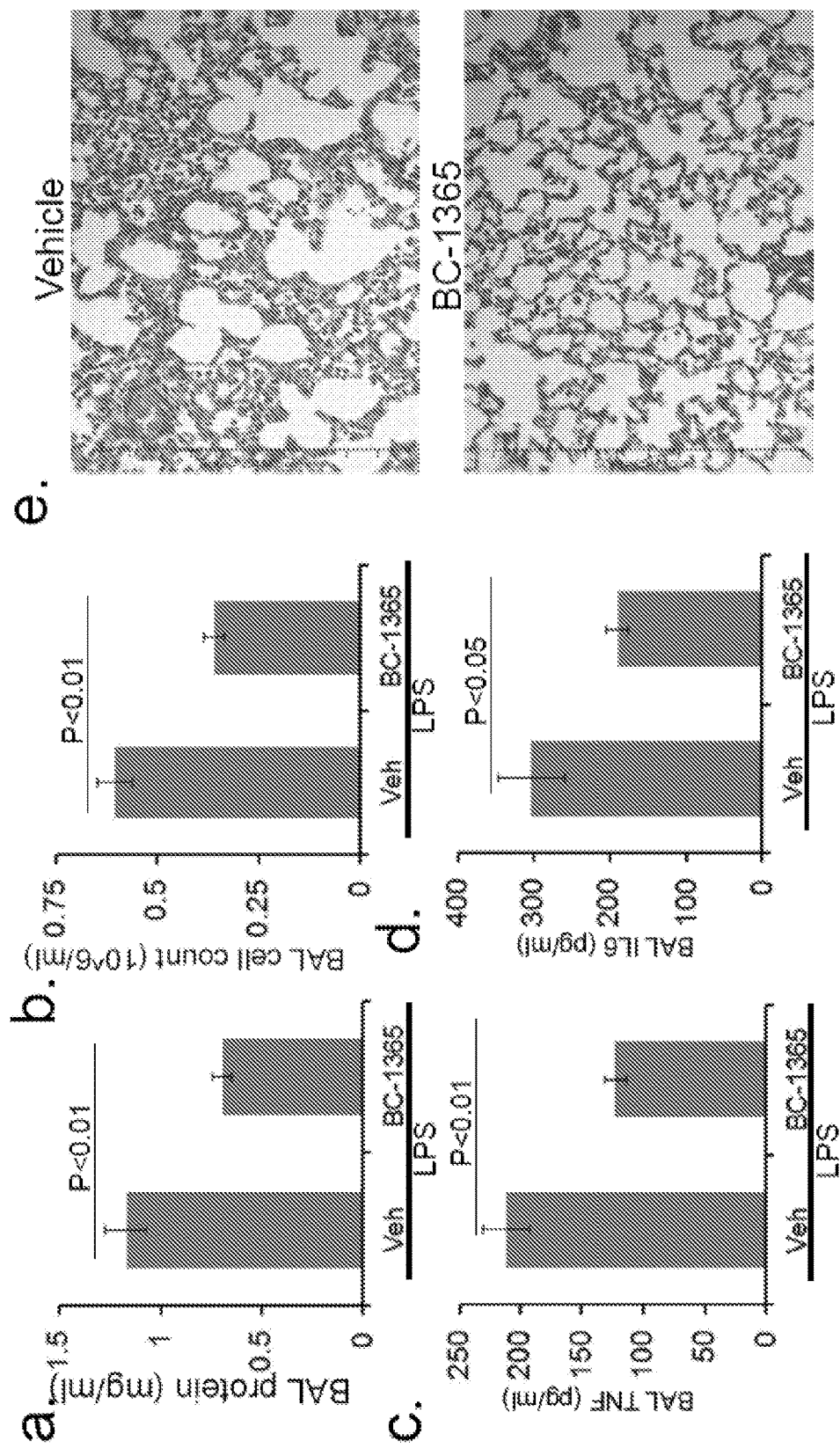
FIGS. 18A-E shows anti-inflammatory activity of a FIEL1 small molecule inhibitor in LPS pneumonia model. C57BL/6J mice were administered i.t. with LPS (E. coli, 3 mg/kg). BC-1365 was given through IP injection (10 mg/kg) at the same time. 18 h later, mice were sacrificed, and lungs were lavaged with saline, harvested, and then homogenized. Lavage protein, cell count and cytokine secretion were measured in (FIGS. 18A-D).
Figure 19:
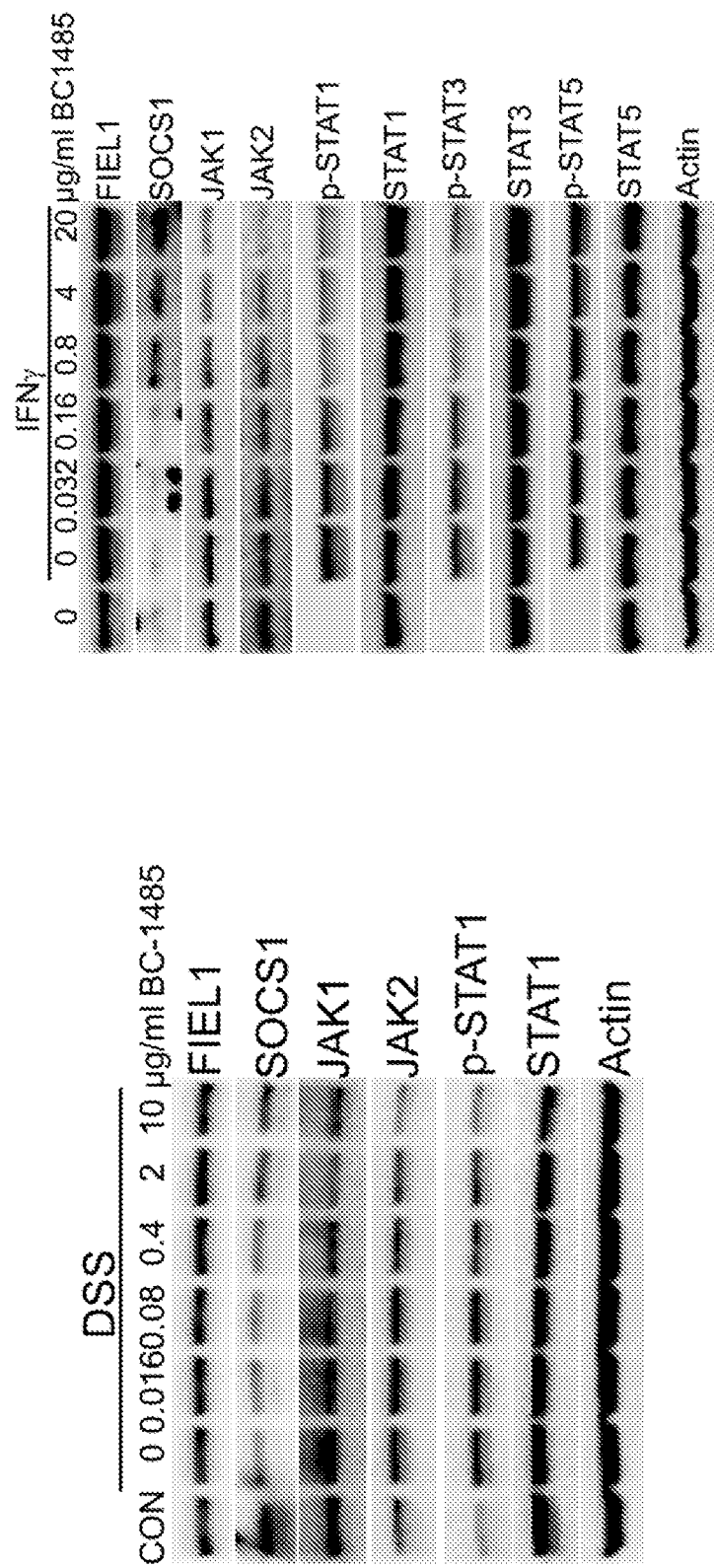
FIG. 19 shows that BC1485 inhibits JAK/STAT pathway through decreasing JAK1 and JAK2, p-Stat1 and p-Stat3 protein levels.

To further assess the anti-fibrotic activity of BC-1485, it was tested in vivo using a bleomycin model. Mice were first challenged with bleomycin (0.05 U i.t.) for up to 21 days. BC-1485 was given in drinking water with an estimated dose of 5 mg/kg/d. BC-1485 significantly decreased BAL protein concentrations, CXCL1, and IL-6 levels (FIGS. 7E, F, FIG. 16A). BC-1485 also significantly decreased BAL total cell counts (FIG. 7G). Specifically, the differential cell counts of BAL cells revealed that the total decrease in inflammatory cells was mostly due to neutrophils and lymphocytes, with the exception of macrophages on day 7 and 21 (FIGS. 16B-D). BC-1485 also significantly improved survival (FIG. 7H). A marked decrease in lung fibrosis in mice treated with the FIEL1 inhibitor BC-1485 as demonstrated by a significant decrease in hydroxyproline content was observed (FIG. 7I). Peribronchiolar and parenchymal fibrosis were also substantially decreased by BC-1485 (FIG. 16E). Decreased lung collagen visualized by Mason Trichrome staining also suggested that BC-1485 ameliorates bleomycin-induced lung injury (FIG. 7J). Hence, small-molecule targeting of the FIEL1/PIAS4 pathway reduced the severity of fibrosis in a preclinical model.

Example 9

BC1485 Inhibits JAK/Stat Pathway

HCT8 cells were pretreated with BC-1485 at different concentrations for 16 h before exposed to DSS (2%, 16 h)

or IFNγ (10 ng/ml, 1 h). Cells were collected and assayed for protein immunoblotting. BC1485 effectively decreases JAK1 and JAK2, p-Stat1 and p-Stat3 protein levels, and thus inhibits the signaling transduction in JAK/STAT pathway.

Example 10

BC1485 Reduces Dextran Sulfate Sodium (DSS) Induced Acute Colonic Inflammation

Figure 20:
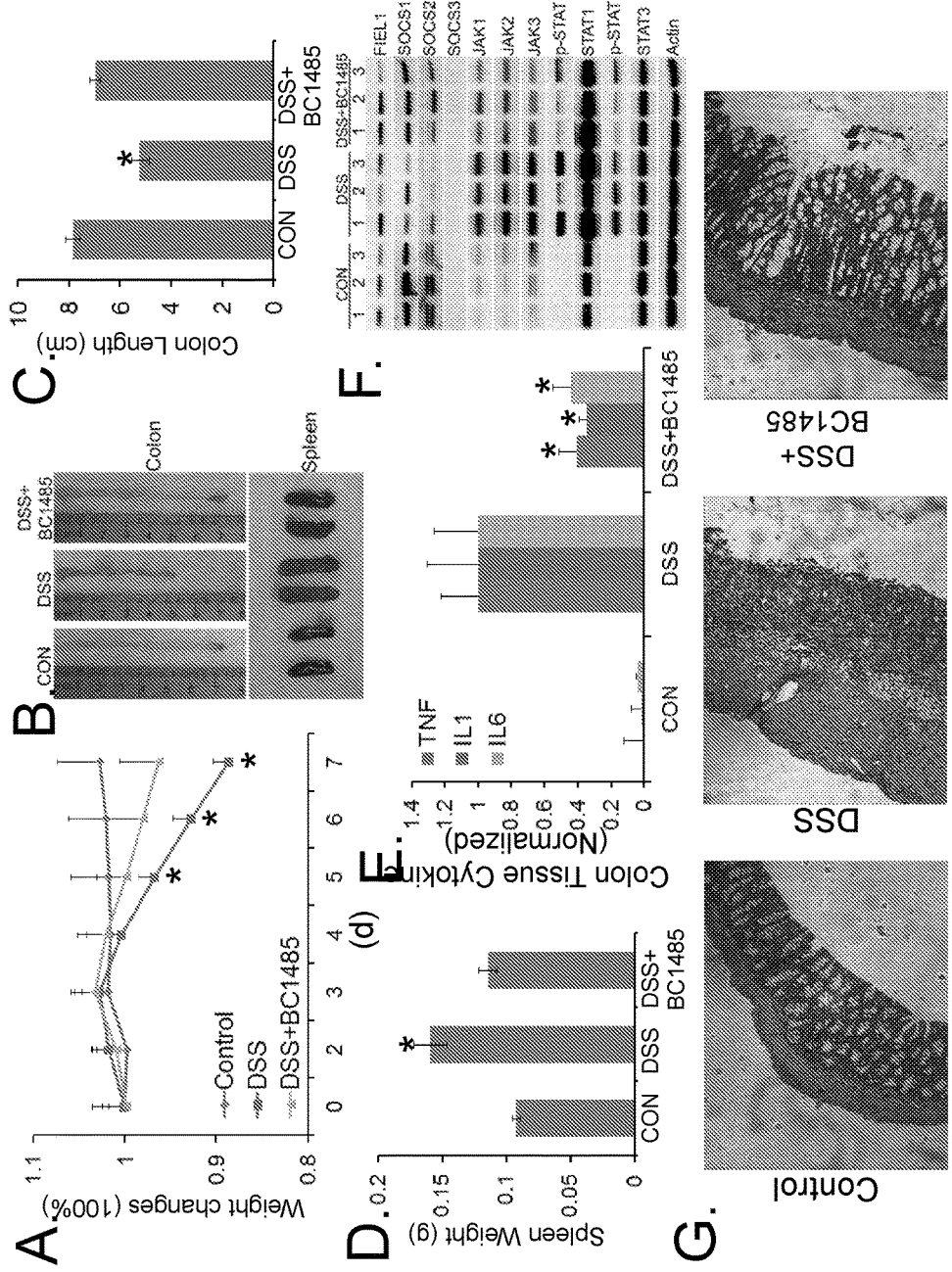
FIG. 20 shows that BC1485 reduces dextran sulfate sodium (DSS) induced acute colonic inflammation. C57BL6 mice were fed with water ad lib containing 2.5% dextran sulfate sodium (DSS) for up to 7 days. Mice were treated with either vehicle (control) or BC-1261 (administered into drinking water at 30 ug/ml, ~5 mg/kg/d dosing). Mice were monitored daily weights were measured and graphed, shown in FIG. 20A. Mice were then euthanized, the length of the colon and weight of the spleen were measured and graphed, shown in FIGS. 20B-D. Colonic tissues were also analysed for TNFα, IL1 and IL6 shown in FIGS. 20E H&E staining was performed on colonic sections. The data in FIG. 20F represent n=6 mice/group, *P<0.05 versus DSS and **P<0.05 versus control. The results shows that BC1485 effectively reduces dextran sulfate sodium induced acute colonic inflammation in mice.

C57BL6 mice were fed with water ad lib containing 2.5% dextran sulfate sodium (DSS) for up to 7 days. Mice were treated with either vehicle (control) or BC-1261 (administered into drinking water at 30 ug/ml, ~5 mg/kg/d dosing). Mice were monitored daily, weights were measured and graphed, shown in FIG. 20A. Mice were then euthanized, the length of the colon and weight of the spleen were measured and graphed, shown in FIGS. 20B-D. Colonic tissues were also analysed for TNFα, IL1 and IL6 shown in FIGS. 20E H&E staining was performed on colonic sections. The data in FIG. 20F represent n=6 mice/group, *P<0.05 versus DSS and **P<0.05 versus control. The results shows that BC1485 effectively reduces dextran sulfate sodium induced acute colonic inflammation in mice.

What is claimed is:

1. A pharmaceutical formulation comprising a compound represented by Formula (I):

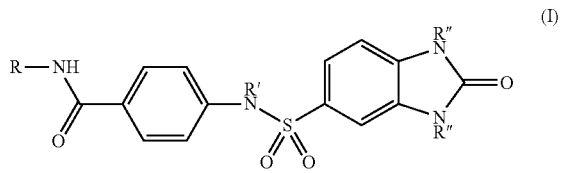

wherein:
R is

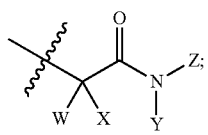

and wherein:
W is selected from the group consisting of H, optionally substituted alkyl, optionally substituted alkoxy, optionally substituted aryl, optionally substituted cycloalkyl, optionally substituted heterocyclic, halogen, amino, and hydroxy;
X is selected from the group consisting of H, optionally substituted alkyl, optionally substituted alkoxy, optionally substituted aryl, optionally substituted cycloalkyl, optionally substituted heterocyclic, halogen, amino, and hydroxy;
Y is selected from the group consisting of H, optionally substituted alkyl, optionally substituted aryl, optionally substituted cycloalkyl, and optionally substituted heterocyclic;
Z is selected from the group consisting of H, optionally substituted alkyl, optionally substituted aryl, optionally substituted cycloalkyl, and optionally substituted heterocyclic;
and wherein Y and Z optionally bind together to form a ring;
R' is selected from the group consisting of H, optionally substituted alkyl, optionally substituted aryl, optionally substituted cycloalkyl, and optionally substituted heterocyclic;

R" is independently selected from the group consisting of H, optionally substituted alkyl, optionally substituted aryl, optionally substituted cycloalkyl, and optionally substituted heterocyclic;
wherein one or more of the alkyl, cycloalkyl, heterocloalkyl, aryl or heteroaryl may be substituted by one or more $C_1$-$C_6$ alkoxy, halogen or deuterium;
or a pharmaceutically acceptable salt thereof, and
a pharmaceutically acceptable excipient.

2. The pharmaceutical formulation of claim 1, wherein:
(a) W is selected from the group consisting of H, optionally substituted alkyl, and optionally substituted aryl;
(b) X is selected from the group consisting of H, optionally substituted alkyl, and optionally substituted aryl, and
(c) W and X cannot both be H.

3. The pharmaceutical formulation of claim 1, wherein:
(a) Y is selected from the group consisting of H, optionally substituted alkyl, and optionally substituted aryl,
(b) Z is selected from the group consisting of H, optionally substituted alkyl, and optionally substituted aryl, and (c) Y and Z cannot both be H.

4. The pharmaceutical formulation of claim 1, wherein R' is H.

5. The pharmaceutical formulation of claim 1, wherein R" is H.

6. The pharmaceutical formulation of claim 1, wherein R is

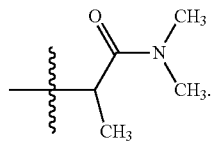

7. The pharmaceutical formulation of claim 1, wherein R is

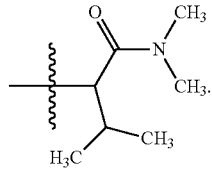

8. The pharmaceutical formulation of claim 1, wherein R is

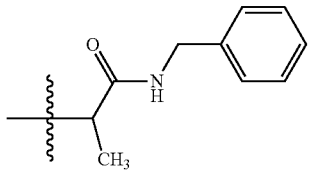

9. The pharmaceutical formulation of claim 1, wherein R is

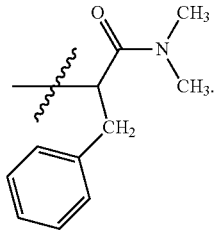 [SMILES: *C(Cc1ccccc1)C(=O)N(C)C]

* * * * *